US008012681B2

(12) United States Patent
Zimmerman et al.

(10) Patent No.: US 8,012,681 B2

(45) Date of Patent: Sep. 6, 2011

(54) METHODS OF MODULATING METASTASIS AND SKELETAL RELATED EVENTS RESULTING FROM METASTASES

(75) Inventors: Deborah Lee Zimmerman, Oakland, CA (US); Rhonda Hansen, San Rafael, CA (US); Jill Winter, Richmond, CA (US); Christoph Reinhard, Indiana, CA (US); Shuling Fang, Castro Valley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 996 days.

(21) Appl. No.: 10/556,765

(22) PCT Filed: May 12, 2004

(86) PCT No.: PCT/US2004/014830

§ 371 (c)(1), (2), (4) Date: Jan. 22, 2008

(87) PCT Pub. No.: WO2004/101764

PCT Pub. Date: Nov. 25, 2004

(65) Prior Publication Data

US 2008/0241067 A1 Oct. 2, 2008

Related U.S. Application Data

(60) Provisional application No. 60/470,006, filed on May 13, 2003, provisional application No. 60/504,324, filed on Sep. 19, 2003.

(51) Int. Cl.
*C12Q 1/68* (2006.01)

(52) U.S. Cl. ....... 435/6; 435/325; 536/24.31; 424/130.1

(58) Field of Classification Search ........................ None
See application file for complete search history.

(56) References Cited

U.S. PATENT DOCUMENTS

| | | | | |
|---|---|---|---|---|
| 5,650,504 | A | 7/1997 | Bartley et al. | |
| 6,927,203 | B1 * | 8/2005 | Kinch et al. | 514/2 |
| 7,192,698 | B1 * | 3/2007 | Kinch et al. | 435/6 |
| 2004/0028685 | A1 | 2/2004 | Kinch et al. | |

FOREIGN PATENT DOCUMENTS

| | | |
|---|---|---|
| WO | WO-02/087555 | 11/2002 |
| WO | WO-03/094859 A2 | 11/2003 |

OTHER PUBLICATIONS

Carles-Kinch et al. Antibody Targeting of the EphA2 Tyrosine Kinase Inhibits Malignant Cell Behavior. Cancer Research 2002, vol. 62: 2840-2847.*

Yoneda. Cellular and Molecular Mechanisms of Breast and Prostate Cancer Metastasis to Bone. European Journal of Cancer, vol. 34, No. 2: 240-245, 1998.*

Branch, A. D. (Feb. 1998). "A Good Antisense Molecule is Hard to Find," *Trends in Biochemical Sciences* 23:45-50.

Carles-Kinch, K. et al. (May 15, 2002). "Antibody Targeting of the EphA2 Tyrosine Kinase Inhibits Malignant Cell Behavior," *Cancer Research* 62:2840-2847.

Crooke, S. T. (1985). "Basic Principles of Antisense Therapeutics" Chapter 1 *In Antisense Research and Application*. Crooke, S. T. ed., Springer:New York, p. 1-50.

Green, D. W. et al. (Jul. 2000). "Antisense Oligonucleotides: An Evolving Technology for the Modulation of Gene Expression in Human Disease," *Journal of the American College of Surgeons* 191(1):93-105.

International Search Report mailed Oct. 20, 2005, for PCT Application No. PCT/US04/14830 filed May 12, 2004, 3 pages.

Jen, K.-Y. et al. (2000). "Suppression of Gene expression by Targeted Disruption of Messenger RNA: Available Options and Current Strategies," *Stem Cells* 18:307-319.

Ross, J. S. et al. (1998). "The HER-2/neu Oncogene in Breast Cancer: Prognostic Factor, Predictive Factor, and Target for Therapy," *Stem Cells* 16:413-428.

Supplementary European Search Report mailed Mar. 19, 2008, for EP Application No. 04751974.9 filed May 12, 2004, 3 pages.

* cited by examiner

*Primary Examiner* — Kimberly Chong

(74) *Attorney, Agent, or Firm* — David A. Carpenter; Patricia Tsao

(57) ABSTRACT

The invention provides, inter alia, models of bone metastasis, methods for identifying agents that modulate skeletal related events and metastasis, methods for modulating skeletal related events and metastases, and methods for detecting skeletal related events and metastases. The methods and models generally comprise co-culturing cancer cells and host cells and comparing biological markers from such co-cultured cells to control cells.

5 Claims, 13 Drawing Sheets

FIG 1

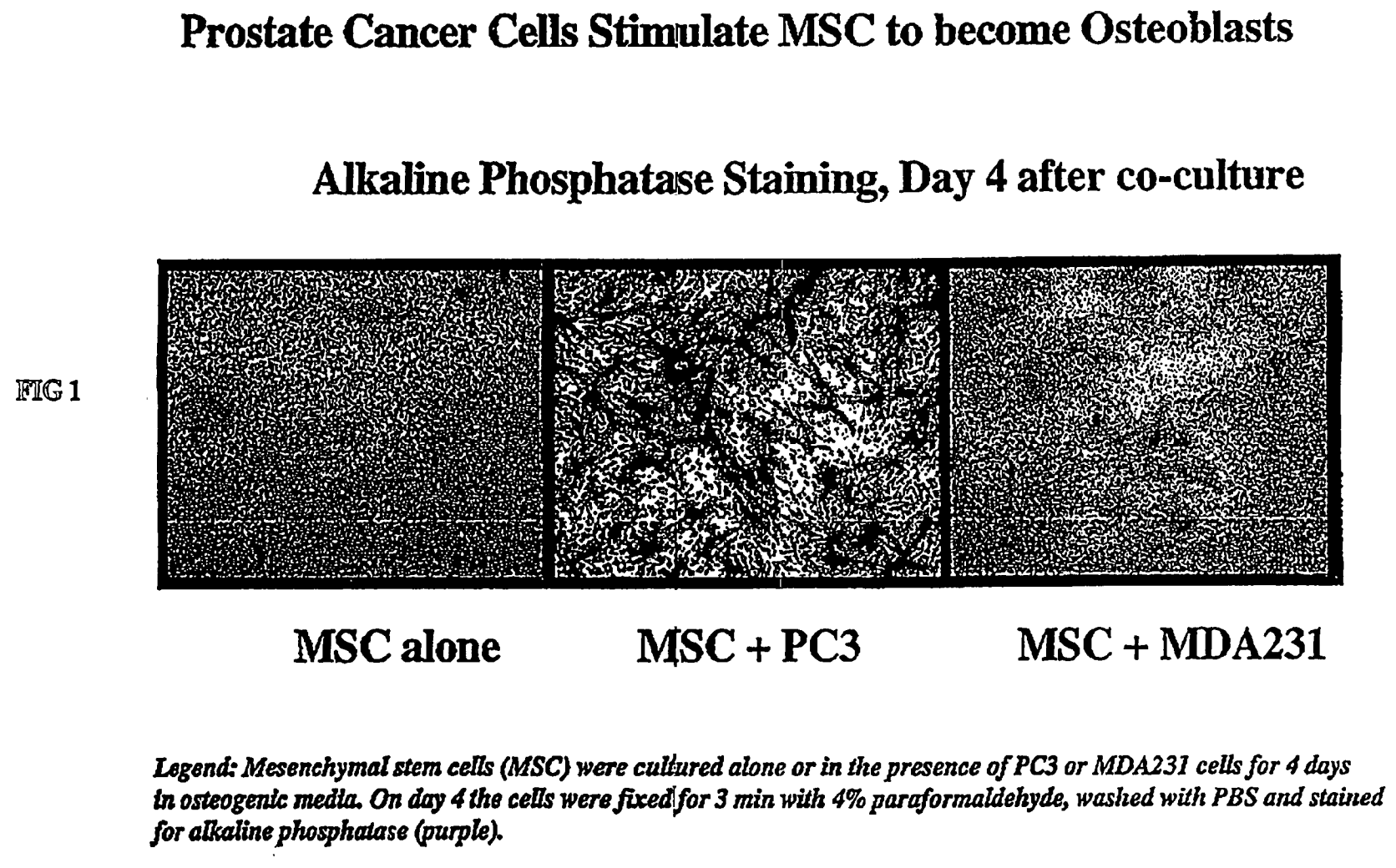

Prostate Cancer Cells Stimulate MSC to become Osteoblasts

Alkaline Phosphatase Staining, Day 4 after co-culture

MSC alone MSC + PC3 MSC + MDA231

*Legend: Mesenchymal stem cells (MSC) were cultured alone or in the presence of PC3 or MDA231 cells for 4 days in osteogenic media. On day 4 the cells were fixed for 3 min with 4% paraformaldehyde, washed with PBS and stained for alkaline phosphatase (purple).*

*Legend: MSC were cultured alone or in the presence of PC3 or MDA231 cells for 4 days in osteogenic media. On day 4 the cells were harvested and assayed for alkaline phosphatase activity.*

OB Co-cultured with Prostate Cancer Cells Produce a Mineralized ECM

Von Kossa Staining, Day 13 after co-culture

*Legend: Mesenchymal stem cells (MSC) were cultured alone or in the presence of LNCaP cells for 13 days in osteogenic media. On day 13 the cells were fixed for 3 min with 4% paraformaldehyde and stained for calcium phosphate with Von Kossa stain.*

FIG 4

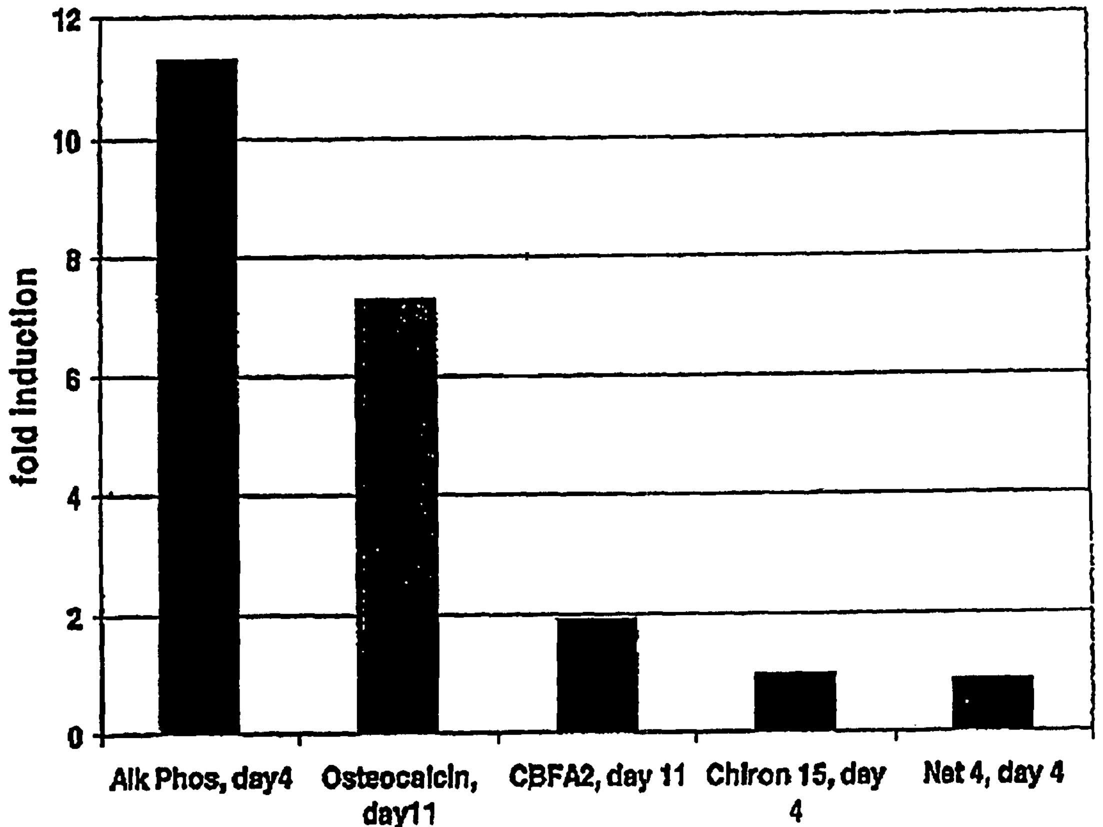

*Legend: Mesenchymal stem cells (MSC) were cultured alone or in the presence of PC3 cells for 4 or 11 days in osteogenic media. At the appropriate time total RNA was prepared from the cells. The RNA was subjected to reverse transcription and analyzed for the expression of specific genes with the Light Cycler. The data is reported as fold induction, or the ratio of expression in the coculture/ expression in MSC alone.*

Scfv 7 recognizes a 130Kd membrane antigen on PC3 cells

Fig. 5

Immunofluoresence

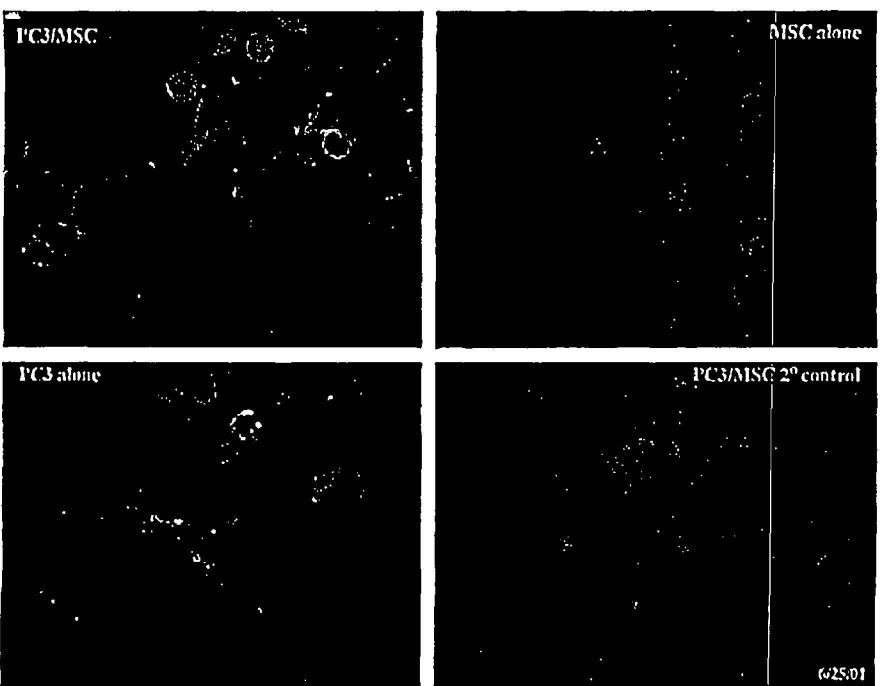

*Legend: PC3 cells expressing GFP were cocultured for 4 days with MSC. The coculture was then fixed and stained with Scfv7 and detected with rhodamine labeled 2° antibody.*

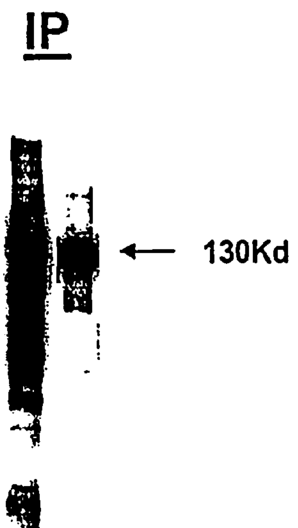

*Legend: PC3 cells were cell-surface biotinylated and lysed. Lysate was loaded directly (lane 1) or immunoprecipitated with Scfv t (lane 2). Samples were run on an SDS-acrylamide gel, transferred to nitrocellulose and probed with HRP-conjugated Strep Avidin.*

Scfv 7 Recognizes EphA2

Figs. 7A and 7B

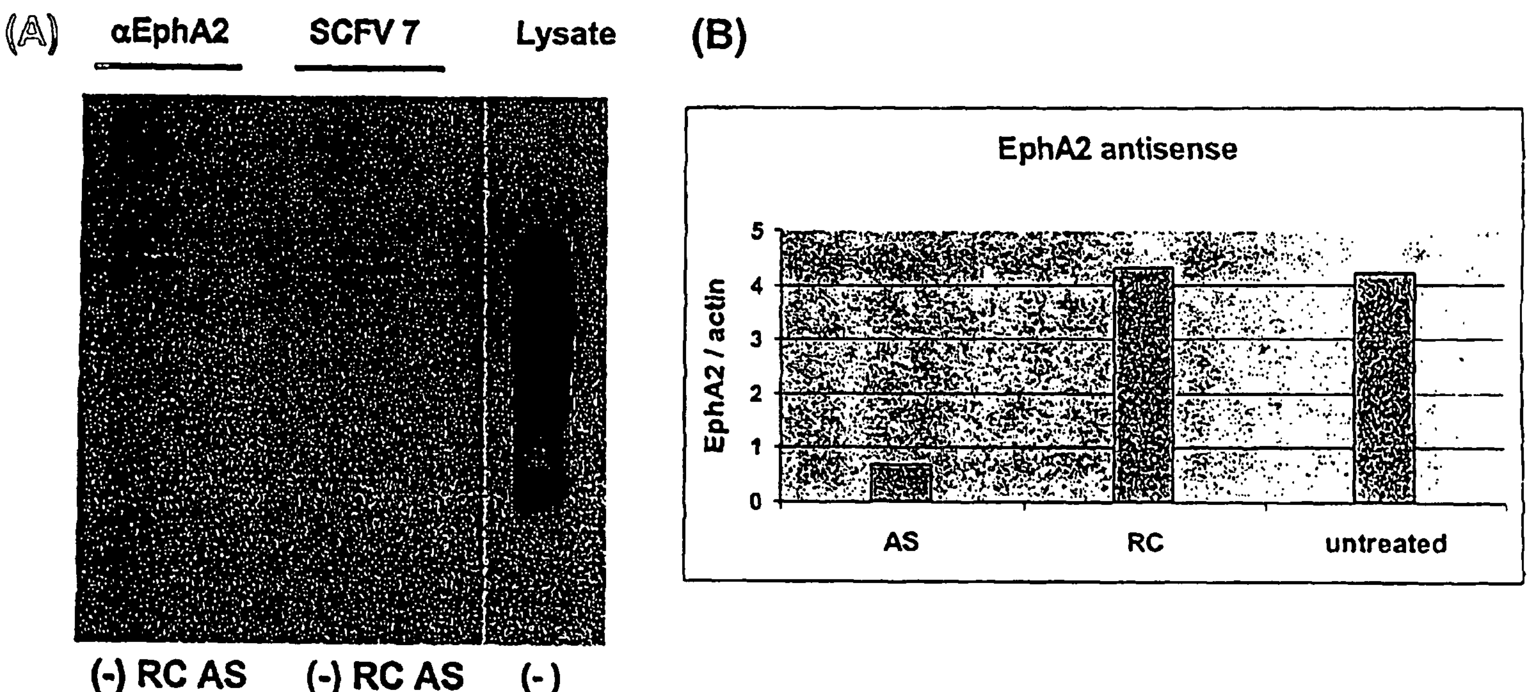

*Legend: PC3 cells were transfected with antisense or reverse control oligos to EphA2. After 3 d in culture the cells were harvested for RNA (B) or were cell-surface biotinylated and lysed (A). (A) Cell lysates were loaded directly or were immunoprecipitated with Scfv 7 or with antibody to EphA2. All samples were run on an SDS-polyacrylamide gel, transferred to nitrocellulose and probed with HRP-conjugated Strep Avidin. (B) Total RNA was prepared subjected to reverse transcription and analyzed by Light Cycler analysis for expression of EphA2 mRNA.*

Figure 8:
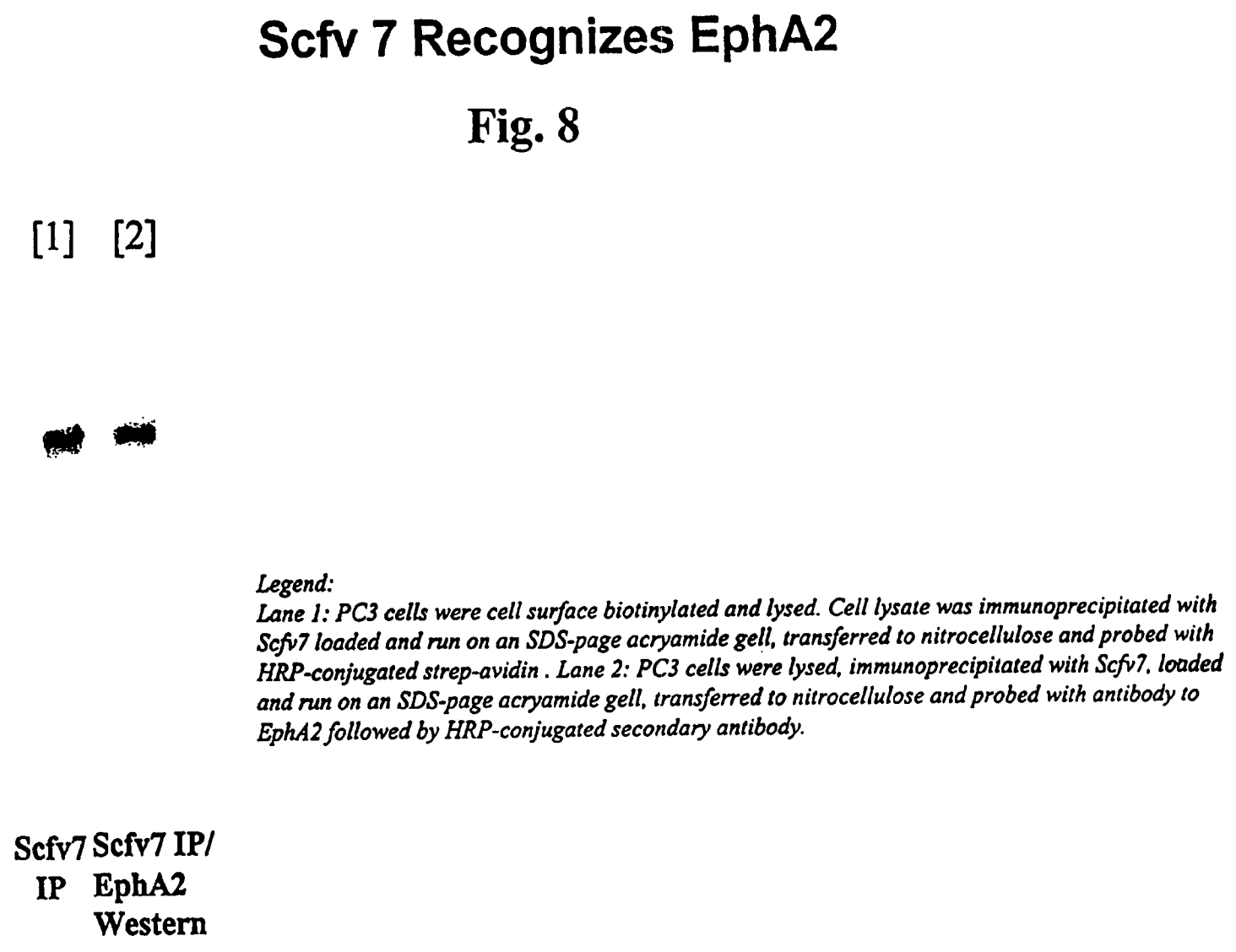

Scfv 7 Recognizes EphA2

Scfv7 IP

Scfv7 IP/ EphA2 Western

*Legend:*
*Lane 1: PC3 cells were cell surface biotinylated and lysed. Cell lysate was immunoprecipitated with Scfv7 loaded and run on an SDS-page acryamide gell, transferred to nitrocellulose and probed with HRP-conjugated strep-avidin . Lane 2: PC3 cells were lysed, immunoprecipitated with Scfv7, loaded and run on an SDS-page acryamide gell, transferred to nitrocellulose and probed with antibody to EphA2 followed by HRP-conjugated secondary antibody.*

EphA2 Antisense Inhibits the Osteoblastic Response

Fig. 9

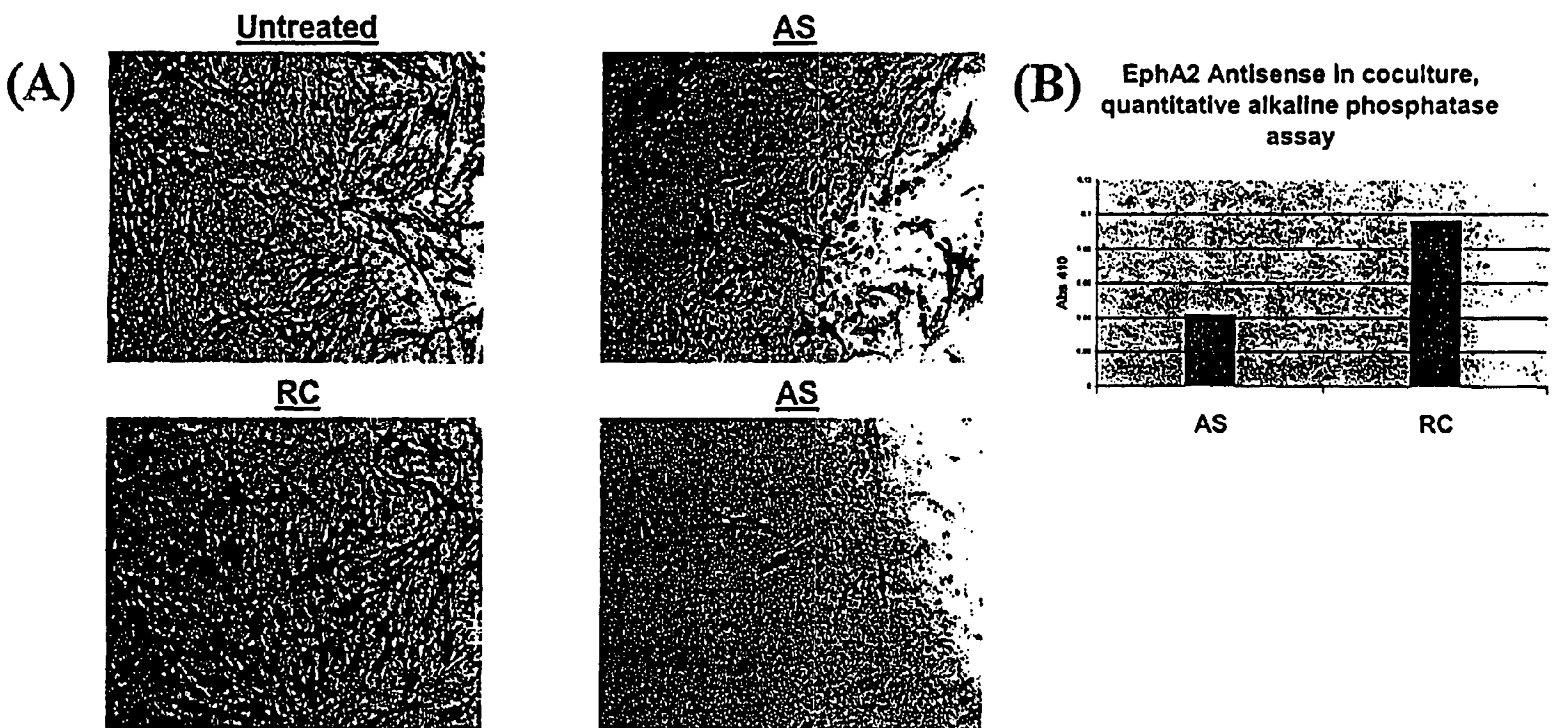

*Legend: On day 1 PC3 cells were plated at a density of 16,000 cells per $cm^2$ in RPMI with 10% FCS and 1x Pen/Strep. On day 2 cells were either untreated (untreated) or were transfected with antisense oligos to EphA2 (AS) or with reverse control oligos (RC). On day 3 the media was changed to osteogenic media and MSC were added to the culture at a density of 10,000 cells/ $cm^2$. The cultures were incubated for another 3d at 37° in 5% $CO_2$. On the third day cells were either fixed and stained for alkaline phosphatase staining (panel (A)) or lysed for quantitative alkaline phosphatase assay s (panel (B)).*

EphA2 is highly expressed in many cancers

Fig. 11

EphA2 is overexpressed in some epithelial cancers

Normal ovary

Ovarian cancer

| Tissue | # positive | Density (++) | Extent (3) |
|---|---|---|---|
| OvCa | 6/6 | 67% | 67% |
| OvN | 6/7 | 0 | 0 |
| PrCa | 17/19 | 76% | 53% |
| PrN | 19/20 | 10% | 37% |
| BrCa | 43/44 | 84% | 80% |
| BrN | 21/22 | 33% | 10% |

Fig. 12

EphA2 mRNA Levels in Normal Tissues vs colon cancer

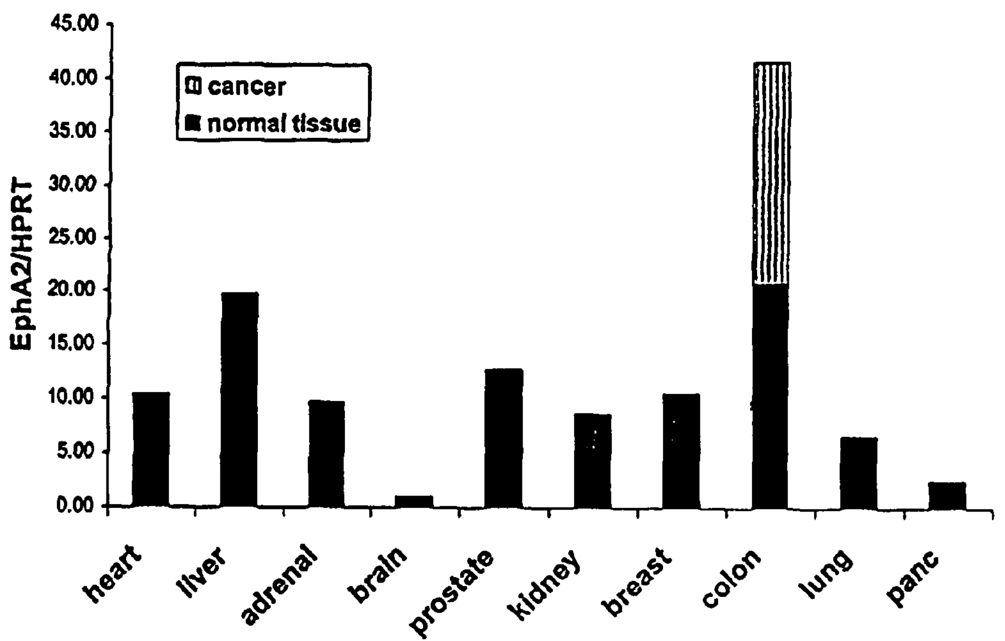

*gend: Total RNA from normal tissues from from multiple individuals was pooled, reverse transcribed and subjected to quantitative PCR ing primers to EpHA2 (black). Amplified RNA from LCM dissected tissue from six cancer and peritumoral normal tissue was reverse transcribed d subjected to quantitative PCR with primers to EphA2. The mRNA levels in the cancer were found to be approximately twice as high as the ritumoral levels in colon cancer patients. Assuming that the levels in the peritumoral samples is similar to the levels in normal colon, then ›hA2 levels in colon cancer are about 2 fold higher than in normal colon and than any other tissue that we tested (grey).*

Fig. 13 Functional Validation: EphA2 Inhibits Matrigel Growth of PC3 cells
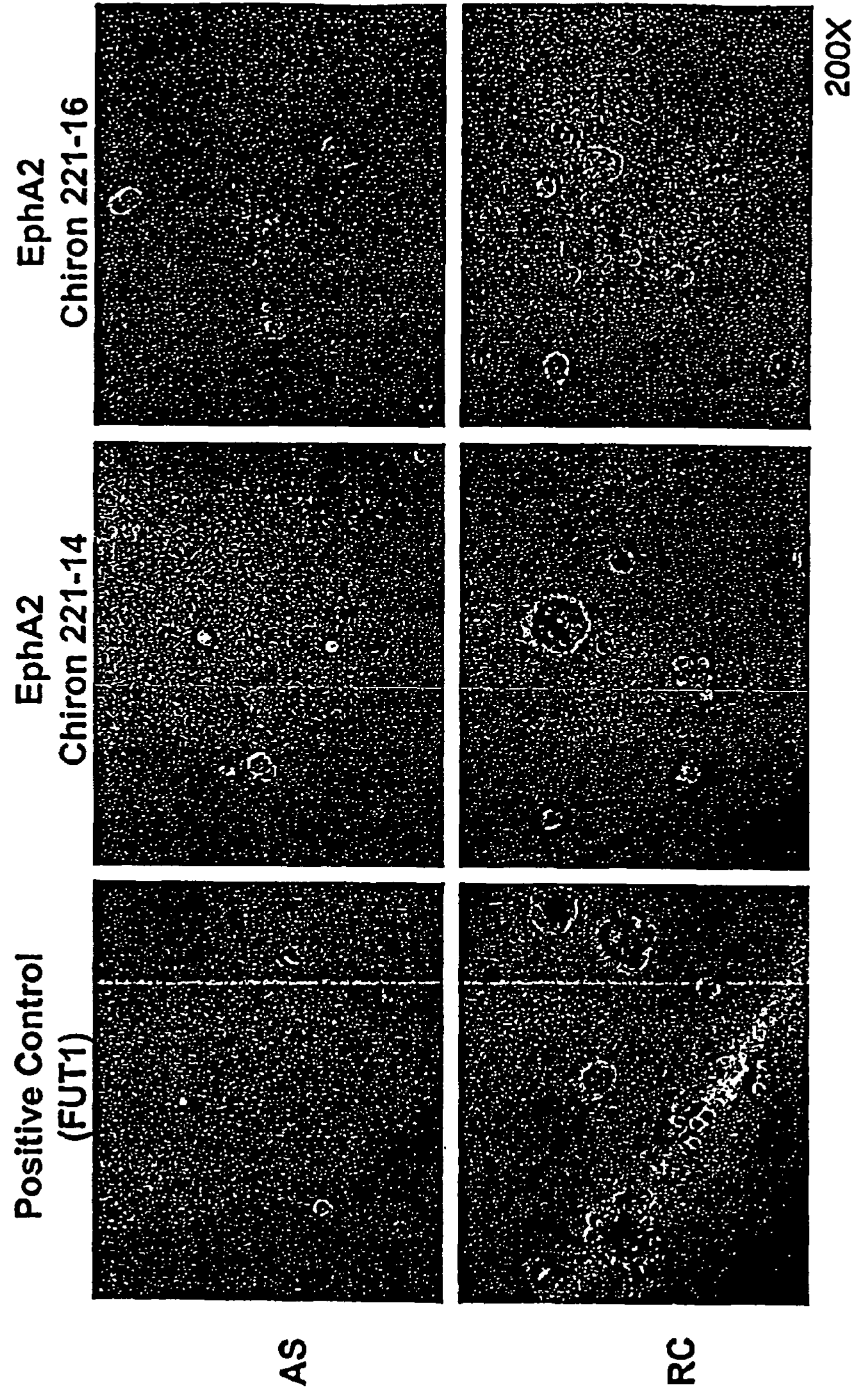
*Legend: PC3 cells were treated with antisense or reverse control oligos to EphA2 then plated on Matrigel with a 3% Matrigel overlay. Pictures were taken after 7d in culture. Positive control for transfection and growth is FUT1.*

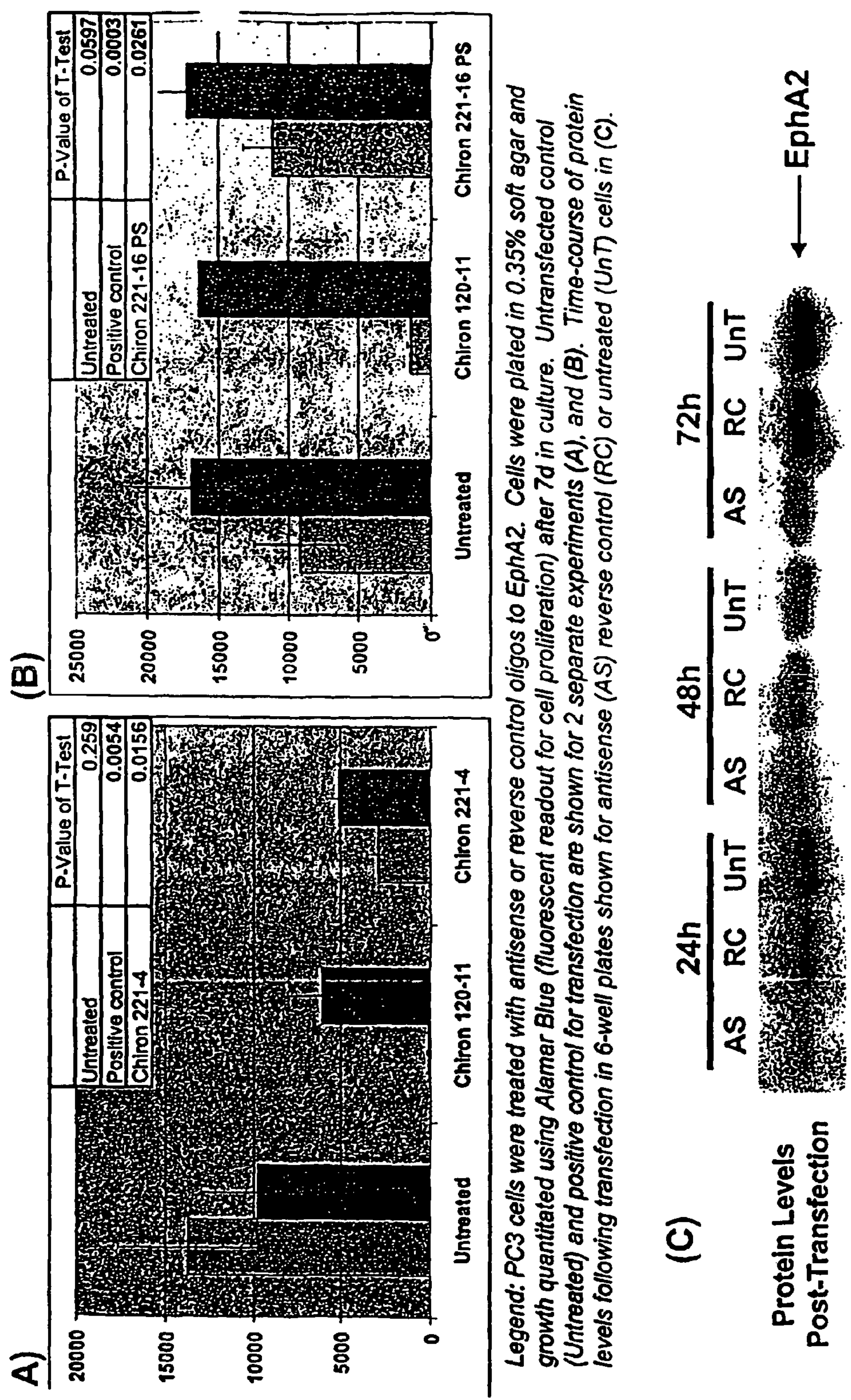

Fig. 14: Functional Validation: EphA2 Inhibits Soft Agar Growth of PC3 cells

*Legend: PC3 cells were treated with antisense or reverse control oligos to EphA2. Cells were plated in 0.35% soft agar and growth quantitated using Alamar Blue (fluorescent readout for cell proliferation) after 7d in culture. Untransfected control (Untreated) and positive control for transfection are shown for 2 separate experiments (A). and (B). Time-course of protein levels following transfection in 6-well plates shown for antisense (AS) reverse control (RC) or untreated (UnT) cells in (C).*

METHODS OF MODULATING METASTASIS AND SKELETAL RELATED EVENTS RESULTING FROM METASTASES

The current application claims priority benefit of U.S. Ser. No. 60/470,006, filed May 13, 2003, and U.S. Ser. No. 60/504,324, filed Sep. 19, 2003, each of which is hereby incorporated by reference in its entirety.

FIELD OF THE INVENTION

The present invention relates generally to the field of oncology. More particularly, the invention relates to methods for modulating skeletal related events and metastases, methods for identifying agents that modulate skeletal related events and metastasis, models of skeletal related events and metastasis, and using said agents to image and/or detect skeletal related events and metastases.

BACKGROUND OF THE INVENTION

Cancer is the second leading cause of death in the United States. Although "cancer" is used to describe many different types of cancer, i.e. breast, prostate, lung, colon, pancreas, each type of cancer differs both at the phenotypic level and the genetic level. The unregulated growth characteristic of cancer occurs when one or more genes acquire mutations and cell growth can no longer be controlled.

Genes are often classified in two classes, oncogenes and tumor suppressor genes. Oncogenes are genes whose normal function is to promote cell growth, but only under specific conditions. When an oncogene gains a mutation and then loses that control, it promotes growth under all conditions. However, it has been found that for cancer to be truly successful the cancer must also acquire mutations in tumor suppressor genes. The normal function of tumor suppressor genes is to stop cellular growth. Examples of tumor suppressors include p53, p16, p21, and APC, all of which, when acting normally, stop a cell from dividing and growing uncontrollably. When a tumor suppressor is mutated or lost, that brake on cellular growth is also lost, allowing cells to now grow without restraints.

Although several genes and their protein products have been identified as being involved in tumorigenesis, the genes that play a role in metastasis are still unclear. Metastasis is an important part of tumorigenesis and is the spreading of the cancer from its primary site of growth to secondary sites that lead to the death of an individual. Examples of types of cancers that often spread to different areas of the body are prostate, breast, lung, and colon.

Most patients originally diagnosed with either prostate or breast cancer develop bone metastases and, at the time of death, most of the tumor burden is found in bone. Cancer has a wide range of bone-related effects. In metastases from breast cancer or from myeloma, the bone-related effect is typically osteoclastic. In contrast, metastases from prostate cancer typically cause osteoblastic effects. Skeletal related events (SREs) are often a result of bone metastases and lead to complications including bone pain, hypercalcemia, pathologic fractures, leukoerythroblastic anemia, bone deformity, and nerve-compression syndrome, among others, thought to be a result of osteolysis. (G. Mundy, Nature (2002), Vol. 2, 584-593). Median survival for patients with metastases to bone is between 2-3 years.

There is some evidence that inhibitors of bone resorption might be useful in inhibiting such complications. Bisphosphonates, pyrophosphate analogs used to treat diseases characterized by bone loss including osteoporosis and Paget's disease, cause a reduction in osteolytic bone lesions as well as a decrease in bone tumor burden. See H. Fleisch, Bisphosphonates In Bone Disease, From The Laboratory To The Patient, 2nd Edition, Parthenon Publishing (1995), which is incorporated by reference herein in its entirety.

A great amount of preclinical and clinical data exists for the bisphosphonate compound alendronate. Evidence suggests that other bisphosphonates including tiludronate, ibandronate, risedronate and zolendronate, have many properties in common with alendronate, including high potency as inhibitors of osteoclastic bone resorption. An older bisphosphonate compound, etidronate, also inhibits bone resorption. There is speculation that existing therapies for inhibiting osteoclastic bone resorption may be effective in treating osteoblastic metastases if the osteoblastic response was dependent on a previous osteoblast activity. Other existing therapies for bone metastases include osteoprotegrin (thought to prevent RANK-L from binding to its receptor and stimulating osteoclasts), RANK-Fc (thought to prevent RANK-L from binding to its receptor and stimulating osteoclasts), PTHrP antibodies, and Vitamin-D analogs (thought to decrease PTHrP production). (G. Mundy, Nature (2002), Vol. 2, 584-593).

Although some studies support the contention that bisphosphonates reduce tumor burden in bone, there is controversy as to whether such inhibitors have the same effect in soft-tissue metastases. Indeed, one study reported that bisphosphonates actually promoted soft-tissue metastasis. (Saarto et al., J. Clin. Oncol. (2001), 19: 10-17).

Several molecules have been shown to be expressed in epithelial cell cancers including breast and prostate cancer. Although EphA2 has been previously shown to participate in oncogenic behavior in breast cancer cells, there are no published reports of a functional role of EphA2 in metastases of cancer to the bone, or in Skeletal Related Events (SREs).

Thus, there is a need to identify genes and gene products that play a role in cancer as well as in cancer metastases and in skeletal related events as well as models of metastasis and SREs. Similarly, there is a need to identify modulators of skeletal related events and metastasis as well as methods for modulating skeletal related events and metastasis. There is a further need to identify methods of imaging/detecting/diagnosing metastases and skeletal related events. The present invention is directed to these, as well as other, important needs.

SUMMARY OF THE INVENTION

The present invention addresses the needs identified above in that it provides, inter alia, models of bone metastasis, methods for identifying molecules that play a role in skeletal related events and metastasis, methods for identifying modulators of skeletal related events and metastasis, methods of imaging/detecting skeletal related events and metastases, and methods for modulating skeletal related events and metastasis.

The present invention also provides methods of simulating the progression of cancer in a patient from primary tumor to metastasis comprising co-culturing one or more host cells with one or more cancer cells for a time sufficient to permit the detection of biological markers indicative of metastasis. In some embodiments, the host and cancer cells are co-cultured in vitro. In some embodiments the host and cancer cells are co-cultured in an animal model. In some embodiments, the animal model is a SCID mouse. In some embodiments the cancer is breast, prostate or colon cancer and the metastasis is to bone. In some embodiments the modulator inhibits metastasis. In some embodiments the host cells are human. In some embodiments the cancer and host cells are isolated from the patient. In some embodiments the methods further comprise the step of identifying one or more genes in said cancer cells whose expression is modulated when co-cultured with said host cells.

Further, the present invention provides methods of simulating the progression from a primary tumor to a metastasis in an in vitro model comprising the steps of co-culturing cancer cells and host cells for a time sufficient to detect evidence of gene expression in said co-culture. In some embodiments the cancer is prostate cancer, breast cancer or colon cancer. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145. In some embodiments, the host cells are isolated from the patient. In some embodiments the co-culturing is in vitro.

Further, the present invention also provides methods for determining the effect of a treatment for a metastatic cancer comprising: (a) administering a modulator to a co-culture of host cells and cancer cells, and (b) comparing biological markers on the co-cultured cells of (a) to biological markers of host and cancer cells co-cultured in the absence of the putative modulator. In some embodiments the modulator inhibits metastasis. In some embodiments the host cells are human. In some embodiments the cancer and host cells are isolated from the patient.

The present invention also provides methods of determining the susceptibility of a patient to a metastasis comprising determining whether biological markers in a first sample, said first sample comprising cancer cells from said patient co-cultured with host cells for a period sufficient to detect said biological markers, correlate with a first control sample comprising cancer cells known to metastasize co-cultured with host cells, wherein a correlation of biological markers in said first sample with biological markers in said first control sample indicates susceptibility of the patient to a metastasis. In some embodiments, the cancer cells known to metastasize are selected from the group consisting of PC3, LNCaP, MDA231, MDA435, HT-29, SW620, HEPG2, and DU 145. In some embodiments, the host cells are isolated from the patient. In some embodiments the co-culturing is in vitro.

The invention also provides methods for determining the susceptibility of a cancer patient to one or more skeletal related events comprising detecting evidence of EphA2 expression in a patient's cancer sample, wherein evidence of EphA2 expression is indicative of the patient's susceptibility to one or more skeletal related events. In some embodiments the metastasis is bone metastasis. In some embodiments the cancer is prostate, breast or colon cancer.

In some embodiments the methods further comprise the step of determining whether the biological markers in said first sample correlate with biological markers in a second control sample, said second control sample comprising host cells co-cultured with cancer cells known not to metastasize, wherein a correlation of biological markers in said first sample with biological markers in said second control sample indicates a reduced susceptibility to a metastasis.

The present invention provides methods of modulating skeletal related events in a cancer patient comprising administering a therapeutically effective amount of one or more EphA2 inhibitors to said patient. In some embodiments the EphA2 inhibitor is an oligonucleotide, a small molecule, a mimetic, a decoy, or an antibody. In some embodiments the inhibitor inhibits EphA2 expression by at least 50%, at least 75%, at least 90%, and preferably at least 95%. In some embodiments the methods further comprise the treatment of the patient with chemotherapy and/or radiation therapy. In some embodiments the methods further comprise the treatment of the patient with a therapeutically effective amount of a bisphosphonate. In some embodiments the metastasis is bone metastasis. In some embodiments the cancer is prostate, breast or colon cancer.

The present invention also provides methods of modulating a metastasis in a patient comprising the steps of: (a) determining if the patient is a candidate for EphA2 therapy as described herein; b) administering one or more EphA2 inhibitors to the patient if the patient is a candidate for EphA2 therapy; and c) treating the patient with conventional cancer treatment if the patient is not a candidate for EphA2 therapy. In some embodiments the methods further comprise the administration of a traditional cancer therapeutic.

In some embodiments the oligonucleotide has a nucleotide sequence of SEQ ID NO: 1 or SEQ ID NO:5. In some embodiments, the oligonucleotide has at least 80%, and preferably at least 90% sequence homology to SEQ ID NO: 1 or SEQ ID NO:5. In some embodiments the oligonucleotide has a nucleotide sequence selected from the group consisting of SEQ ID NO:3, SEQ ID NO:72, SEQ ID NO:73, SEQ ID NO:74, SEQ ID NO:75, SEQ ID NO:76, SEQ ID NO:77, SEQ ID NO:78, SEQ ID NO:79 or SEQ ID NO:80. In some embodiments the oligonucleotide binds under stringent hybridization or moderate hybridization conditions to a nucleotide sequence of SEQ ID NO:1 or SEQ ID NO:5.

In some embodiments the oligonucleotides are complementary to a nucleic acid molecule that encodes a peptide having a sequence of SEQ ID NOs:12-71.

In some embodiments the small molecule is an organic molecule with a molecular weight no greater than 5 kilodaltons.

In some embodiments the antibody is a humanized antibody. In some embodiments, the antibody binds to EphA2 with an affinity of at least $1\times10^8$ Ka.

In some embodiments the skeletal related event is selected from the group consisting of bone fracture, radiation for bone pain or fracture prevention or treatment, spinal cord compression, bone surgery, bone metastasis, or hypercalcemia of malignancy.

The present invention also provides methods of modulating a metastasis in a patient comprising administering to said patient a therapeutically effective amount of the pharmaceutical compositions of the present invention. In some embodiments the methods further comprise the administration of a traditional cancer therapeutic.

Further, the present invention provides methods of modulating metastasis in a cancer patient comprising administering a therapeutically effective amount of an EphA2 inhibitor to said patient. In some embodiments the EphA2 inhibitor is an oligonucleotide, a small molecule, a mimetic, a decoy, or an antibody. In some embodiments the inhibitor inhibits EphA2 expression by at least 50%, at least 75%, at least 90%, and preferably at least 95%. In some embodiments the methods further comprise the administration of a traditional cancer therapeutic. In some embodiments the methods further comprise the treatment of the patient with chemotherapy and/or radiation therapy. In some embodiments the methods further comprise the treatment of the patient with a therapeutically effective amount of a bisphosphonate. In some embodiments the metastasis is bone metastasis. In some embodiments the cancer is prostate cancer, breast cancer or colon cancer.

In some embodiments the oligonucleotides of the present invention have a nucleotide sequence of SEQ ID NO: 1 or SEQ ID NO:5. In some embodiments, the oligonucleotides have at least 80%, and preferably at least 90% sequence homology to SEQ ID NO: 1 or SEQ ID NO:5. In some embodiments the oligonucleotide has a nucleotide sequence selected from the group consisting of SEQ ID NO:3, SEQ ID NO:72, SEQ ID NO:73, SEQ ID NO:74, SEQ ID NO:75, SEQ ID NO:76, SEQ ID NO:77, SEQ ID NO:78, SEQ ID NO:79 or SEQ ID NO:80. In some embodiments the oligonucleotides bind under stringent hybridization or moderate hybridization conditions to a nucleotide sequence of SEQ ID NO:1 or SEQ ID NO:5.

In some embodiments the small molecule is an organic molecule with a molecular weight no greater than 5 kilodaltons.

In some embodiments the antibody is a humanized antibody. In some embodiments, the antibody binds to EphA2 with an affinity of at least $1\times10^8$ Ka.

In some embodiments the antibodies of the present invention recognize at least one region of EphA2 sequence, wherein the regions correspond to SEQ ID NOs:12-71. In some embodiments the antibody is a monoclonal antibody, a polyclonal antibody, a chimeric antibody, a humanized antibody, a single-chain antibody, or a Fab fragment. In some embodiments the antibodies of the present invention are labeled. In some embodiments the label is an enzyme, radioisotope, or fluorophore. In some embodiments the antibodies having a binding affinity less than about $1\times10^5$ $K_a$ for a polypeptide other than EphA2.

In some embodiments the present invention provides an isolated cell that produces an antibody that recognizes at least one portion of EphA2 sequence corresponding to SEQ ID NOs:12-71. In some embodiments the isolated cell is a hybridoma.

The present invention further provides methods of identifying a patient susceptible to a metastasis comprising comparing biological markers of a cancer cell from a patient, said cancer cell co-cultured with one or more host cells, to biological markers of control cancer cells co-cultured with one or more host cells. In some embodiments, the control cancer cells are indicative of a non-metastasizing cancer cell. In some embodiments, the control cancer cells are indicative of a metastasizing cancer cell. In some embodiments the methods further comprise the step of determining whether a biological marker in the cancer cell from said patient correlates to a positive control or to a negative control. In some embodiments the cancer and host cells are isolated from the patient.

The present invention also provides methods for determining the susceptibility of a cancer patient to a metastasis comprising detecting evidence of EphA2 expression in a patient's cancer sample, wherein evidence of EphA2 expression is indicative of the patient's susceptibility to a metastasis.

Further the present invention provides methods for determining the susceptibility of a cancer patient to a metastasis comprising detecting evidence of EphA2 expression in a co-culture of a cancer and a host cell from said patient, wherein evidence of EphA2 expression is indicative of the patient's susceptibility to a metastasis. In some embodiments, evidence of EphA2 expression is detected by measuring EphA2 RNA. In some embodiments, evidence of EphA2 expression is detected by measuring EphA2 expression products. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145.

The present invention also provides methods of determining the appropriateness of EphA2 therapy for a cancer patient comprising detecting evidence of EphA2 expression in a patient's cancer sample, wherein evidence of EphA2 expression is indicative of a patient for whom EphA2 therapy is appropriate.

The present invention further provides methods for determining the appropriateness of EphA2 therapy for a cancer patient comprising detecting evidence of EphA2 expression in a co-culture of a cancer and host cell from said patient, wherein evidence of EphA2 expression is indicative of a patient for whom EphA2 therapy is appropriate. In some embodiments the cancer cells are selected from the group consisting of PC3, LNCaP, MDA231, MDA435, HT-29, SW620, HEPG2, and DU 145.

The present invention also provides methods of identifying genes modulated during bone metastasis comprising comparing an expression profile of co-cultured cancer and host cells to a control expression profile of cancer cells. In some embodiments the modulated gene is EphA2. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145. In some embodiments the cancer and host cells are isolated from the patient. In some embodiments, the present invention also provides genes identified by such methods.

The present inventions further provides methods of identifying genes modulated during skeletal related events comprising comparing an expression profile of co-cultured cancer and host cells to a control expression profile of cancer cells. In some embodiments the modulated gene is EphA2. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145. In some embodiments the cancer and host cells are isolated from the patient.

Further, the present invention also provides methods of identifying molecules on the surface of cancer cells comprising the steps of: (a) co-culturing cancer cells and host cells; (b) adding phage expressing scfvs to the co-culture under conditions allowing binding of the scfvs to the cancer cells; (c) isolating the cancer cells bound to scfvs; and (d) characterizing the scfvs, thereby identifying the molecule on the surface of the cancer cell. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145. In some embodiments the cancer and host cells are isolated from a patient.

The present invention also provides methods for identifying modulators of metastasis comprising contacting a co-culture of cancer and host cells with a putative modulator and detecting the presence or absence of biological markers indicative of metastasis, wherein the absence of biological markers indicative of metastasis in said co-culture relative to a control is indicative of an modulator of metastasis. In some embodiments the metastasis is EphA2-related metastasis. In some embodiments the host and/or cancer cells comprise EphA2. In some embodiments the biological markers are selected from the group consisting of modulation of calcium deposits, osteocalcin levels, alkaline phosphatase levels, tartrate acid resistant phosphatase activity, expression profiles, evidence of cell-cell interaction, osteoclast activity, osteoblast activity, growth hormone, prolactin, collagen, procollagen, osteopontin, osteonectin, bone sialoprotein, tartrate acid resistant phosphatase, alpha 2-HS glycoprotein, hydroxyproline, hydroxylysine glycosides, pyridinium crosslinks, osteocalcin, or the formation of a mineralized extracellular matrix, cell-to-cell membrane exchange. In some embodiments the cancer cells are prostate, breast or colon cancer cells. In some embodiments the cancer and host cells are isolated from the patient. The present invention also provides modulating compounds identified by such methods.

In some embodiments the modulator is selected from the group consisting of an oligonucleotide, an antibody, a mimetic, a decoy receptor, or a small molecule.

In some embodiments the cancer and host cells are cocultured in a mouse xenograft. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145.

The present invention further provides methods for detecting a metastasis in a patient comprising administering to the patient a composition comprising an EphA2 modulator linked to an imaging agent and detecting the localization of the imaging agent in the patient. In some embodiments the composition comprises an anti-EphA2 antibody conjugated to an imaging agent. In some embodiments the imaging agent is $^{18}$F, $^{43}$K, $^{52}$Fe, $^{57}$Co, $^{67}$Cu, $^{67}$Ga, $^{77}$Br, $^{87}$MSr, $^{86}$Y, $^{90}$Y, $^{99}$MTc, $^{111}$In, $^{123}$I, $^{125}$I, $^{127}$Cs, $^{129}$Cs, $^{131}$I, $^{132}$I, $^{197}$Hg, $^{203}$Pb, or $^{206}$Bi.

The present invention also provides methods for quantifying the amount of EphA2 present in a sample comprising contacting the sample with a composition comprising an EphA2 modulator linked to an imaging agent and quantifying the imaging agent.

The present invention further provides methods for modulating pain in a cancer patient comprising administering a therapeutically effective amount of an EphA2 inhibitor to said patient. In some embodiments the EphA2 inhibitor is selected from the group consisting of a small molecule, an oligonucleotide, a mimetic, a decoy receptor, or an antibody.

The present invention also provides methods for modulating the interaction of a cancer cell and a host cell in a patient comprising administering a therapeutically effective amount of an EphA2 inhibitor to said patient. In some embodiments the host cell is selected from the group consisting of stem cells, osteoblasts, osteoclasts, stromal cells, and bone marrow cells. In some embodiments the EphA2 inhibitor is selected from the group consisting of a small molecule, an oligonucleotide, a mimetic, a decoy receptor, or an antibody. In some embodiments the interaction between said cancer cell and said host cell is modulated by an anti-EphA2 antibody. In some embodiments the cancer cells are selected from the group consisting of PC3, LNCaP, MDA231, MDA435, HT-29, SW620, HEPG2, and DU 145.

The present invention also provides compositions comprising human host cells, human cancer cells, and osteogenic media comprising about $10^{-7}$M dexamethasone, about 0.05 mM ascorbate phosphate, and about 10 mM betaglycerophosphate.

The present invention further provides pharmaceutical compositions comprising an EphA2 modulator and one or more pharmaceutically acceptable carriers. In some embodiments the EphA2 modulator is selected from the group consisting of an oligonucleotide, an antibody, a mimetic, a decoy receptor, or a small molecule. In some embodiments the composition is a sterile injectable.

The present invention further provides methods of modulating one or more SREs in a patient comprising administering to said patient a therapeutically effective amount of the pharmaceutical compositions of the present invention.

The present invention also provides methods of identifying a patient susceptible to EphA2 therapy comprising the steps of: (a) administering to the patient a composition comprising an EphA2 modulator linked to an imaging agent; and (b) detecting the presence or absence of evidence of EphA2 expression in said patient, wherein the presence of evidence of EphA2 expression in said patient is indicative of a patient who is a candidate for EphA2 therapy and the absence of evidence of EphA2 expression in said patient is indicative of a patient who is not a candidate for EphA2 therapy.

Further, the present invention also provides methods of identifying a patient susceptible to EphA2 therapy comprising the steps of: (a) administering to the patient a composition comprising an EphA2 modulator linked to an imaging agent; and (b) detecting the presence or absence of clinical endpoints indicative of a SRE or metastasis in said patient, wherein the presence of clinical endpoints indicative of a SRE or metastasis is indicative of a patient who is a candidate for EphA2 therapy and the absence of evidence of clinical endpoints indicative of a SRE or metastasis is indicative of a patient who is not a candidate for EphA2 therapy. In some embodiments, the clinical endpoint is selected from the group consisting of fractures, spinal cord compression, and hypercalcemia. In some embodiments the clinical endpoints are detected radiologically. In some embodiments clinical endpoints are measured by detecting levels of cross-linked amino acids.

The present invention further provides methods for inhibiting anchorage-independent cell growth in a patient comprising administering to the patient a therapeutically effective amount of an EphA2 inhibitor. In some embodiments, the cancer cells are selected from the group consisting of breast, prostate, colon, and melanoma cells.

The present invention also provides methods for inhibiting migration of cancer cells in a patient comprising administering to the patient a therapeutically effective amount of an EphA2 inhibitor. In some embodiments, the cancer cells are selected from the group consisting of breast, prostate, colon, and melanoma cells. In some embodiments the methods further comprise the administration of a traditional cancer therapeutic.

Further, the present invention provides methods for inhibiting adhesion of cancer cells comprising administering to the patient a therapeutically effective amount of an EphA2 inhibitor. In some embodiments, the cancer cells are selected from the group consisting of breast, prostate, colon, and melanoma cells. In some embodiments the cancer cells are selected from the group consisting of PC3, LNCaP, MDA231, MDA435, HT-29, SW620, HEPG2, and DU 145. In some embodiments the methods further comprise the administration of a traditional cancer therapeutic. In some embodiments the cancer and host cells are isolated from the patient.

In some embodiments the methods are performed in vitro.

Further, the present invention also provides methods of expressing an anti-EphA2 antibody in a CHO or myeloma cell. In some embodiments the anti-EphA2 antibody inhibits bone skeletal related events in a patient having a bone metastasis. The methods comprise expressing a nucleic acid encoding the anti-EphA2 antibody in CHO or myeloma cells. In some embodiments the anti-EphA2 antibody comprises SEQ ID NO:7.

The present invention also provides pharmaceutical compositions comprising one or more antibodies that bind EphA2. In some embodiments the antibody inhibits bone skeletal related events in a patient having a bone metastasis. In some embodiments the one or more antibodies recognize distinct epitopes of EphA2.

The present invention also provides pharmaceuticals composition comprising one or more antibodies that bind EphA2. In some embodiments the antibodies are identified according to the methods of the present invention.

The present invention further provides methods of expressing an anti-EphA2 antibody in a CHO or myeloma cell. In some embodiments the anti-EphA2 antibody is identified by testing for its effectiveness for treating metastasis in bone according to the present invention.

These and other aspects of the present invention will be elucidated in the following detailed description of the invention.

BRIEF DESCRIPTION OF THE DRAWINGS

FIG. 1 depicts alkaline phosphatase staining in cells at day 4. The left panel depicts mesenchymal stem cells (MSC) alone. The middle panel depicts MSC and PC3 cells in co-culture. The right panel depicts MSC and MDA231 cells in co-culture. The increase in staining depicted in the middle panel is indicative of bone metastasis and an osteoblastic response to bone metastasis.

FIG. 4 depicts Light Cycler analysis of gene expression. Mesenchymal stem cells were cultured alone or in the presence of PC3 cells for 4 or 11 days in osteogenic media. After the appropriate time total RNA was prepared from the cells. The RNA was subjected to reverse transcription and analyzed for the expression of the specific genes with the Light Cycler. The data is reported as fold induction, or the ratio of expression in the co-culture to expression in MSC alone.

FIG. 5 depicts PC3 cells expressing GFP and MSC cells cultured alone or together. Samples were cultured for 4 days. Co-cultures were fixed and stained with Scfv7 and detected with a rhodamine labeled secondary antibody.

FIG. 6 depicts immunoprecipitation of a protein from PC3 cells. PC3 cells were cell-surface biotinylated and then lysed. The lysate was loaded directly (lane 1) or immunoprecipitated with scfv 7 (lane 2). Samples were run on a SDS-polyacrylamide gel, transferred to nitrocellulose and probed with HRP-conjugated streptavidin.

FIGS. 7A and 7B depict the effect of antisense oligonucleotide on EphA2 expression. PC3 cells were transfected with antisense or reverse control oligonucleotides to EphA2. After 3 days in culture the cells were harvested for RNA or were cell-surface biotinylated and lysed. For FIG. 7A cell lysates were loaded directly or were immunoprecipitated with Scfv7 or with antibody to EphA2. Samples were run on a SDS-PAGE gel, transferred to nitrocellulose, and probed with HRP-conjugated streptavidin. For FIG. 7B, total RNA was prepared, subjected to reverse transcription, and analyzed by Light Cycler analysis for expression of EphA2 mRNA.

FIG. 8 depicts Western blots of PC3 lysates. Lane 1: PC3 cells were cell surface biotinylated and lysed. Cell lysate was immunoprecipitated with Scfv7, loaded and run on a SDS-PAGE gel, transferred to nitrocellulose, and probed with HRP-conjugated streptavidin. Lane 2: PC3 cells were lysed, immunoprecipitated with Scfv7, loaded and run on a SDS-PAGE gel, transferred to nitrocellulose, and probed with antibody to EphA2 followed by a secondary HRP-conjugated antibody.

FIG. 9 depicts the effect of EphA2 antisense oligonucleotides on the osteoblastic response. PC3 cells were plated on day 1 at a density of 16000 cells per $mm^2$ in RPMI with 10% FCS (fetal calf serum) and 1× Pen/Strep. On day 2 cells were either untreated or were transfected with antisense oligonucleotides to EphA2 (AS) or with reverse control oligonucleotides (RC). On day 3 the media was changed to osteogenic media and MSC were added to the culture at a density of 10000 cells per $mm^2$. The cultures were incubated for another 3 days at 37° C. in 5% $CO_2$. On the third day cells were either fixed and stained for alkaline phosphatase (panel A) or lysed for quantitative alkaline phosphatase assays (panel B).

FIG. 11 depicts the overexpression of EphA2 in some epithelial cancers. The left panel compares normal and cancer ovarian cancer samples analyzed using immunohistochemistry. The right panel sets forth statistics relating to cancerous and non-cancerous samples.

FIG. 12 depicts EphA2 mRNA levels in normal tissues and in colon cancer samples. Total RNA from multiple donors was pooled, reverse transcribed, and subjected to quantitative PCR using primers to EphA2 (black). Amplified RNA from laser capture microdissected (LCM) tissue from six cancer and peritumoral normal tissue was reverse transcribed and subjected to quantitative PCR with primers to EphA2. The mRNA levels in the cancer samples were found to be approximately twice as high as the peritumoral levels in colon cancer patients. Assuming the levels in the peritumoral samples is similar to the levels in normal colon, then EphA2 levels in colon cancer are about 2-fold higher than in normal colon and than any other tissue tested.

FIG. 13 depicts the inhibition of PC3 growth in Matrigel by EphA2 antisense oligonucleotides. PC3 cells were treated with antisense or reverse control oligonucleotides to EphA2 then plated on Matrigel with a 3% Matrigel overlay (221-14 is SEQ ID NO:9; 221-16 is SEQ ID NO:10). Images were recorded after 7 days in culture. The positive control for transfection and growth was FUT1 (SEQ ID NO:11).

FIGS. 14 A-C depict the inhibition of PC3 growth in soft agar by Matrigel by EphA2 antisense oligonucleotides. PC3 cells were treated with antisense or reverse control oligonucleotides to EphA2. Cells were plated in 0.35% soft agar and the growth was quantified using Alamar Blue (fluorescent readout for cell proliferation) after 7 days in culture. Untransfected control (untreated) and positive controls of transfection are shown for experiments A and B. Time-course of protein levels following transfection in 6-well plates are shown in FIG. 14 C for antisense (AS), reverse control (RC), or untreated cells (UnT).

DETAILED DESCRIPTION

Figure 2:
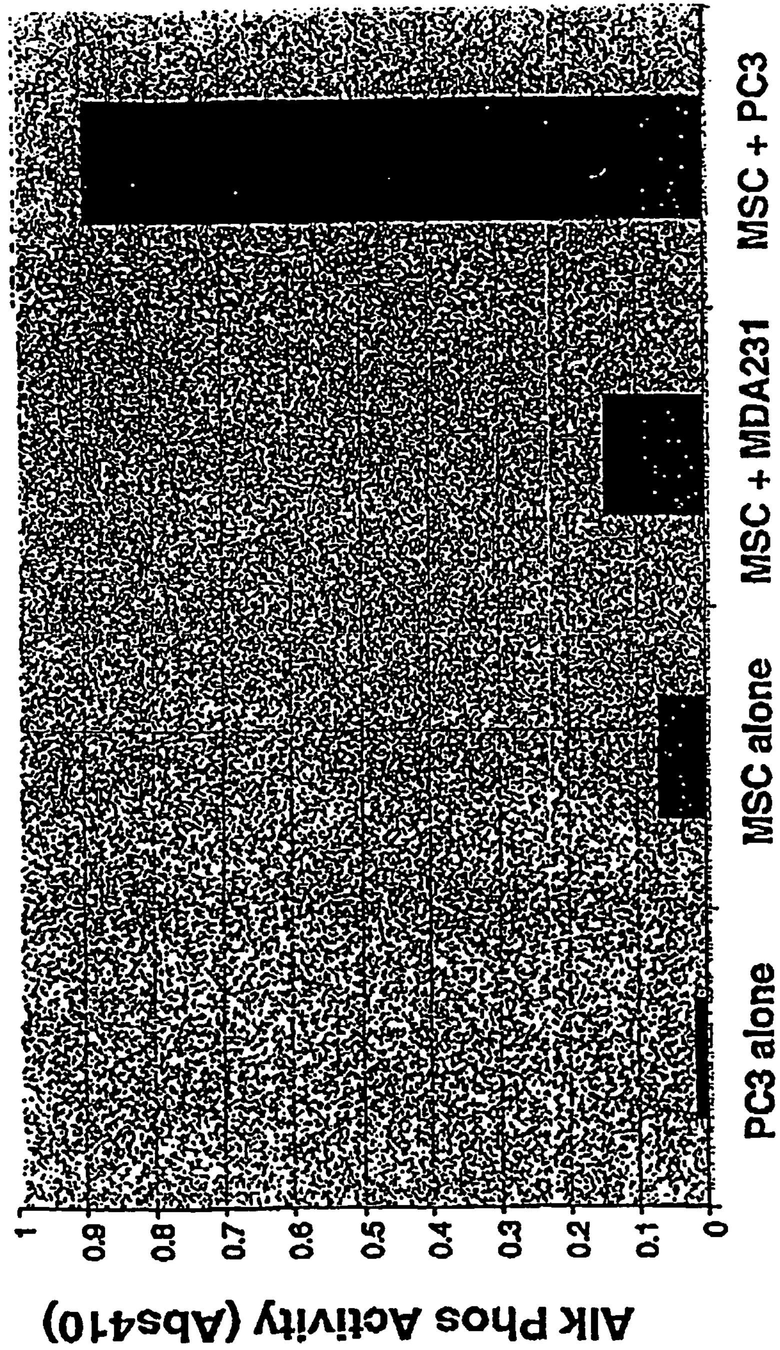
FIG. 2 depicts alkaline phosphatase activity. MSC were cultured alone or in the presence of PC3 or MDA231 cells for 4 days in osteogenic media. On day 4 the cells were harvested and assayed for alkaline phosphatase activity. Alkaline phosphatase activity appeared to be highest when MSC and PC3 cells were co-cultured.

Various definitions are used throughout this document. Most words have the meaning that would be attributed to those words by one skilled in the art. Words specifically defined either below or elsewhere in this document have the meaning provided in the context of the present invention as a whole and as are typically understood by those skilled in the art.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

As used in this specification and the appended claims, the singular forms "a," "an" and "the" include plural references unless the content clearly dictates otherwise. Thus, for example, reference to "an antibody" includes a mixture of two or more such antibodies.

As used herein, the term "about" refers to +/−30%, +/−20%, +/−10%, or +/−5% of a value.

The terms "polypeptide" and "protein", are used interchangeably and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the term "susceptible" refers to patients for whom EphA2 therapy is an acceptable method of treatment, i.e., patients who are likely to respond positively. Cancer patients susceptible to EphA2 therapy express high levels of EphA2 relative to those patients not susceptible to EphA2 therapy. Cancer patients who are not good candidates for EphA2 therapy include cancer patients with tumor samples that lack or have lower levels of EphA2 in or in their cancer cells.

As used herein, the term "host cell" refers to a non-cancerous cell derived from a patient and includes without limitation stem cells, osteoblasts, osteoclasts, stromal cells, bone marrow cells, and the like.

The term "stem cell" is used herein to refer to a mammalian cell that has the ability both to self-renew, and to generate differentiated progeny (see, for example, Morrison et al. (1997) Cell 88:287-298). Stem cells include but are not limited to, mesenchymal stem cells, hematopoietic stem cells, neural crest stem cells, placental stem cells, embryonic stem cells, and mesodermal stem cells, among others. Mesenchymal stem cells (MSC) are pluripotential blast cells found inter alia in bone marrow, blood dermis and periosteum and are capable of differentiating into any of the specific types of mesenchymal stem or connective tissue cells, including adipose, osseous (including osteoblasts) cartilaginous, elastic, and fibrous connective tissues. Although stem cells are generally present in very low numbers in bone marrow, a process for isolating, purifying and greatly enriching these cells in cultures is disclosed in U.S. Pat. No. 5,486,359, which is herein incorporated by reference in its entirety.

As used herein, the term "cancer cells" refers to cells that are transformed. These cells can be isolated from a patient who has cancer, or be cells that are transformed in vitro to become cancerous. Cancer cells can be derived from many types of samples including any tissue or cell culture line. In some embodiments the cancer cells are hyperplasias, tumor cells, or neoplasms. In some embodiments, the cancer cells are isolated from breast, prostate, leukemia, colon, melanoma, lung, brain, liver, pancreas, and lymphoma cancers. In some embodiments, the cancer cells are taken from established cell lines that are publicly available. In some preferred embodiments, the cancer cells are PC3, LNCaP, MDA231, MDA435, HT-29, SW620, HEPG2, and DU 145. In some embodiments, cancer cells are isolated from pre-existing patient samples or from libraries comprising cancer cells. In some embodiments, cancer cells are isolated and then implanted in a different host, e.g., in a xenograft. In some embodiments cancer cells are transplanted and used in a SCID mouse model. In some embodiments, the cancer is prostate, colon, or breast cancer.

As used herein, the term "transformed" refers to any alteration in the properties of a cell that is stably inherited by its progeny. In some preferred embodiments, "transformed" refers to the change of normal cell to a cancerous cell, e.g., one that is capable of causing tumors. In some embodiments, a transformed cell is immortalized. Transformation can be caused by a number of factors, including viral infection, mutations in oncogenes and/or tumor suppressor genes, and or any other technique that changes the growth and/or immortilization properties of a cell.

As used herein, the term "skeletal related event", or "SRE" refers to a physiological event in the skeletal system resulting from a tumor metastasis to bone or from a bone cancer. SREs include without limitation, pathological fractures, spinal cord compression, radiation therapy for pain relief or to treat or prevent pathological fractures or spinal cord compression, hypercalcaemia, and surgery to bone.

As used herein, the term "metastasis" refers to a cancer which has spread to a site distant from the origin of the cancer, e.g. from the primary tumor. Sites of metastasis include without limitation, the bone, lymph nodes, lung, liver, and brain. In some preferred embodiments, the cancer is prostate cancer or breast cancer and metastasis is to the bone.

As used herein, the term "clinical endpoint" refers to a measurable event indicative of a metastasis, preferably to bone, or of a SRE. Clinical endpoints include without limitation, time to first SRE, fractures, spinal cord compression, hypercalcemia, quality of life, and pain. Other endpoints include without limitation biomarkers, urinary output, serum alkaline phosphatase, formation of new bone, radiographic criteria for bony response or progression, and bone mineral density. Those skilled in the art are credited with the ability to determine and measure clinical endpoints. Methods of measuring clinical endpoints are known to those of skill in the art. Examples of such methods are provided in U.S. Pat. No. 5,283,197, U.S. Pat. No. 5,538,853, and U.S. Pat. No. 5,589,346, each of which is incorporated by reference. The most commonly measured bone related markers include calcium, hydroxyproline, alkaline phosphatase, procollagen Type I and its cleavage products, osteocalcin, and bone collagen peptides that include crosslinked amino acids. The crosslinked amino acids include pyridinoline, deoxypyridinoline, hydroxy lysyl pyridinoline, lysyl pyridinoline, n-telopeptide, and the peptides that contain the former molecules. In some embodiments, markers are measured in serum or in urine. In some embodiments, clinical endpoints are detected radiologically.

As used herein, the term "osteogenic" media refers to a solution in which precursor bone cells or bone cells are incubated. In some embodiments the media promotes stem cells to differentiate into cells that are in the bone lineage.

As used herein, the term "bone lineage" refers to a cell that can become part of a bone or is involved in bone physiology. Examples of cells that are included in the bone lineage include osteoclasts, osteoblasts, chondrocytes, and the like.

As used herein, the terms "bone disease" and "bone disorder" refer to a disease or disorder which affects the skeletal system. Bone diseases/disorders include, without limitation, osteoporosis, osteopetrosis, Paget's disease, Osteogenesis Imperfecta, Thyrotoxic Bone Disease, periprosthetic bone loss or osteolysis, hypercalcemia of malignancy, McCune-Albright syndrome, and the like.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, and saccharides.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, proliferation, secretion, adhesion, apoptosis, cell-to-cell signaling, and the like. In the context of "modulating metastasis" the term refers to affecting the rate, amount or degree of metastasis present in a patient. In some embodiments, the methods will completely inhibit metastasis. In other embodiments, the methods will decrease the amount of metastasis. In other embodiments, the methods will prevent metastasis. In the context of SREs, "modulating SRE" refers to affecting the rate, amount or degree of SRE. In some embodiments, the methods will completely inhibit SREs. In other embodiments, the methods will decrease the degree of SRE.

As used herein, the term "modulator" refers to a composition that modulates metastasis and/or one or more SREs. In some embodiments the modulator is a small molecule, an antibody, a mimetic, a decoy receptor or an oligonucleotide. In some embodiments the modulator acts by blocking ligand binding or by competing for a ligand-binding site. In some embodiments the modulator blocks expression of a gene product involved in SREs and/or bone metastasis. In some embodiments the modulator blocks a physical interaction of two or more biomolecules involved in SREs or metastases. In some embodiments the modulator is an inhibitor.

As used herein, the term "N-terminus" refers to the first 10 amino acids of a protein.

As used herein, the term "C-terminus" refers to the last 10 amino acids of a protein.

As used herein, the term "small molecule" refers to an organic or inorganic non-polymer compound that has a molecular weight that is less than about 10 kilodaltons. In some embodiments, the small molecule has a molecular weight that is less than about 9, about 8, about 7, about 6, about 5, about 4, about 3, about 2, about 1 kilodaltons. Examples of small molecules include peptides, oligonucleotides, organic compounds, inorganic compounds, and the like.

As used herein, the term "culturing" refers to growing cells in vitro, in vivo, or ex vivo. Methods of culturing cells are well known to those skilled in the art.

As used herein, the term "co-culture" refers to growing two or more cell types together. Such techniques are well known to those of skill in the art. Cancer cells and host cells are co-cultured for a time sufficient to detect biological markers and is, therefore, related to the biological marker being measured and the technique for measurement. Those of skill in the art are credited with the ability to determine the time period of such culture sufficient to detect such biological markers. In some embodiments, the cancer cells and host cells are co-cultured for about 1 to about 20 days. In some preferred embodiments, the cells are co-cultured for about 10 to about 15 days. In some more preferred embodiments, the cells are co-cultured for about 11 to about 14 days. In some embodiments, co-culturing occurs in vitro. In some embodiments, co-culturing occurs in vivo or ex vivo. In some preferred embodiments, cells are co-cultured in a xenograft host.

As used herein the term "biological marker" refers to markers that are indicative of SREs and/or metastasis and include, without limitation, a modulation of alkaline phosphatase activity, an modulation of calcium deposits as measured by Von Kossa staining, a modulation of RNA or mRNA of the osteocalcin gene, a modulation in RNA or mRNA of the alkaline phosphatase gene, a modulation of tartrate acid resistant phosphatase activity, and the like. Biological markers also include expression profiles (including gene expression profiles, protein expression profiles, RNA expression profiles, mRNA expression profiles, and the like) and biological activities including but not limited to evidence of cell-cell interaction including evidence of membrane exchange between a host cell and a cancer cell.

As used herein, the term "cell-cell interaction" refers to an interaction between two or more cells. In some embodiments, the interaction between the cells leads to a cell signal. Cell-cell interaction can be detected via a number of methods known to those of skill in the art, including, without limitation, the observation of membrane exchange between co-cultured, pre-labeled cells, labeled, for example, with different fluorescent membrane stains including PKH26 and PKH67 (Sigma).

In some embodiments, the biological marker relates to bone physiology. Biological markers relating to bone physiology include, without limitation, osteoclast activity, osteoblast activity, alkaline phosphatase activity, and calcium deposits, growth hormone, prolactin, collagen, procollagen, osteopontin, osteonectin, bone sialoprotein, tartrate acid resistant phosphatase (TRAP), alpha 2-HS glycoprotein, hydroxyproline, hydroxylysine glycosides, pyridinium crosslinks, osteocalcin, and the like. In some embodiments, the biological marker is an expression profile. In some embodiments, the biological marker is alkaline phosphatase activity and is measured by staining the cells for the phosphatase activity or using an enzymatic assay. In some embodiments, the biological marker is analyzed by visualizing calcium deposits in the cell culture using Von Kossa stain. In some embodiments, the biological marker is the formation of a mineralized extracellular matrix or evidence of cell-to-cell membrane exchange.

As used herein the term "indicative of metastasis" refers to a biological marker which correlates with metastasis. Similarly, the term "indicative of SRE" refers to a biological marker which correlates with SREs. Those of skill in the art can readily determine whether biological markers correlate with SREs and/or metastasis. In some embodiments, a determination as to whether a biological marker correlates to a SRE and/or a metastasis is made by comparing an experimental sample to negative and positive controls. If the experimental sample correlates most closely with a negative control (a sample previously determined to be of a cell-type not likely to lead to a SRE or to metastasize), the sample is not indicative of metastasis. If the sample correlates most closely with a positive control (a sample previously determined to be of a cell-type likely to lead to an SRE or to metastasize), the sample is indicative of a SRE or a metastasis, respectively.

As used herein, the phrase, "expression profile" refers to a biochemical profile of a cell and is generally measured by detecting evidence of gene expression (i.e. gene expression profile). The gene expression profile is often measured by the amount of mRNA present in the cell. However, an expression profile can also include the level of the protein or other biological markers linked to a specific gene. Methods of measuring the levels of such biological markers present in a system are well-known to those of skill in the art and include without limitation nucleic acid subtraction techniques including representational difference analysis and differential display analysis, microchip analysis, SAGE, and the like. In some embodiments of the present invention the gene expression profile of a cell that is treated with an agent is compared to the gene expression profile of the same type of cell that has not been treated with the agent. For example, to analyze gene expression at the RNA or mRNA level, RNA and/or mRNA is isolated from the cells. The levels of specific genes can be analyzed using techniques well known to those of ordinary skill in the art, including, without limitation, microchip analysis, serial analysis of gene expression (SAGE), differential display, and the like. The technique that is used is not essential to identify the genes whose expression is modulated during bone metastasis. Once an expression profile is obtained, the expression profile is compared to an expression profile from cells that were not co-cultured in osteogenic media (control expression profile). The control expression profile may be determined prior to, contemporaneously with, or after determination of the co-culture expression profile. Further, the control expression profile may be determined by reference to publicly available data concerning expression profiles. Genes or gene products determined to be present in increased levels in the control expression profile compared to the co-culture expression profile are "down-regulated", while genes or gene products determined to be present in decreased levels in the control expression profile compared to the co-culture expression profile are "up-regulated".

As used herein, the term "control expression profile" refers to an expression profile for a population of cancer cells that has not been co-cultured with host cells.

As used herein, the term "co-culture expression profile" refers to an expression profile for a population of cancer cells and host cells that have been co-cultured.

In some embodiments, expression profiles are determined by measuring protein levels. It is well known to one of ordinary skill in the art to determine and compare protein expression levels between two groups of cells. The cells are treated as above, but instead of isolating RNA or mRNA, the proteins are isolated and analyzed to determine the proteins that have been modulated during bone metastasis. Expression profiles may be determined in the absence or presence of other compositions, including, without limitation, putative modulators, known modulators, growth factors, and combinations and subcombinations thereof.

As used herein, the term "detecting" means to establish, discover, or ascertain evidence of an activity (for example, gene expression) or biomolecule (for example, a polypeptide). Methods of detection are well known to those of skill in the art. For example, methods of detecting polynucleotides include, but are not limited to PCR, Northern blotting, Southern blotting, RNA protection, and DNA hybridization (including in situ hybridization). Methods of detecting polypeptides include, but are not limited to, Western blotting, ELISA, enzyme activity assays, slot blotting, peptide mass fingerprinting, electrophoresis, and immunochemistry, and immunohistochemistry. Other examples of detection methods include, but are not limited to, radioimmunoassay (RIA), chemiluminescence immunoassay, fluoroimmunoassay, time-resolved fluoroimmunoassay (TR-FIA), two color fluorescent microscopy, or immunochromatographic assay (ICA), all well known by those of skill in the art. In some preferred embodiments of the present invention, polynucleotide expression is detected using PCR methodologies and polypeptide production is detected using ELISA technology.

As used herein, the term "evidence of gene expression" refers to any measurable indicia that a gene is expressed. Evidence of gene expression may be gained from methods including, but not limited to, PCR, FISH, ELISA, or Western blots.

The term "domain" as used herein refers to a structural part of a biomolecule that contributes to a known or suspected function of the biomolecule. Domains may be coextensive with regions or portions thereof and may also incorporate a portion of a biomolecule that is distinct from a particular region, in addition to all or part of that region.

As used herein, the term "antibody" refers to monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof. Antibody fragments, including Fab, Fab', F(ab')2, scfv, and Fv are also provided by the invention. Antibodies may, in some preferred embodiments, be monoclonal, humanized, primatized, single chain, or chimeric antibodies.

In addition to chimeric and humanized antibodies, fully human antibodies can derived from transgenic mice having human immunoglobulin genes (see, e.g., U.S. Pat. Nos. 6,075,181, 6,091,001, and 6,114,598, all of which are incorporated herein by reference), or from phage display libraries of human immunoglobulin genes (see, e.g. McCafferty et al., *Nature,* 348:552-554 (1990). Clackson et al., *Nature,* 352:624-628 (1991) and Marks et al., *J. Mol. Biol.,* 222:581-597 (1991)).

Monoclonal antibodies can be prepared using the method of Kohler et al (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas fo expression, antibodies can be produced in a cell line such as a CHO or myeloma cell lines, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. *Immunol.* 147:8; Banchereau et al. (1991) *Clin. Immunol. Spectrum* 3:8; and Banchereau et al. (1991) Science 251:70; all of which are herein incorporated by reference.

Fragments of the antibodies are suitable for use in the methods of the invention so long as they retain the desired affinity of the full-length antibody. Thus, a fragment of an anti-ephA2 antibody will retain the ability to bind to the EphA2 cell-surface antigen expressed on a human cell, particularly to EphA2 on the cell surface of EphA2-expressing cancer cells. Such fragments are characterized by properties similar to the corresponding full-length antagonist anti-EphA2 antibody, that is, the fragments will specifically bind a human EphA2 antigen expressed on the surface of a human cell.

Anti-EphA2 antibodies or antibody fragments thereof may be conjugated prior to use in the methods of the present invention. Methods for producing conjugated antibodies are known in the art. Thus, the anti-EphA2 antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) *Nucl. Med. Bio.* 18:589-603, herein incorporated by reference.

Further, an antibody (or fragment thereof) may be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-alpha, interferon-beta, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known. See, for example, WO 2004010957 A2; Amon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316.

Methods of the invention are directed to the use of Anti-EphA2 antibodies to treat subjects (i.e., patients) having tumors that have caused skeletal related events that express EphA2.

The term "specific for," when used to describe antibodies of the present invention, indicates that the variable regions of the antibodies of the invention recognize and bind target polypeptides exclusively by virtue of measurable differences in properties including binding affinity, despite the possible existence of localized sequence identity, homology, or similarity between the target protein and other polypeptides). Those skilled in the art readily understood that such specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art, as discussed in Harlow et al. (Eds.), Antibodies: A Laboratory Manual; Cold Spring Harbor Laboratory; Cold Spring Harbor, N.Y. (1988), Chapter 6.

Antibodies are defined to be "specifically binding" if: 1) they exhibit a threshold level of binding activity, and/or 2) they do not significantly cross-react with known related polypeptide molecules. The binding affinity of an antibody can be readily determined by one of ordinary skill in the art, for example, by Scatchard analysis (Scatchard, Ann. NY Acad. Sci. 51: 660-672, 1949). In some embodiments the antibodies of the present invention bind to their target epitopes or mimetic decoys at least $10^3$, at least $10^4$, at least $10^5$, and at least $10^6$ fold higher than to other known members of the Eph or Eck family.

In some embodiments, the antibodies of the present invention do not specifically bind to known related polypeptide molecules, for example, if they bind EphA2 polypeptide but not known related polypeptides using a standard Western blot analysis (Ausubel et al.). Examples of known related polypeptides include, without limitation, other members of the Ephrin protein family such as EphA5 (Ephrin receptor A5), EphB2 (Ephrin receptor B2), EphB4 (Ephrin receptor B4), and the like. In some embodiments antibodies may be screened against known related polypeptides to isolate an antibody population that specifically binds to EphA2 polypeptides. For example, antibodies specific to human EphA2 polypeptides will flow through a column comprising Ephrin family polypeptides (with the exception of EphA2) adhered to insoluble matrix under appropriate buffer conditions. Such screening allows isolation of polyclonal and monoclonal antibodies non-crossreactive to closely related polypeptides (Antibodies: A Laboratory Manual, Harlow and Lane (eds.), Cold Spring Harbor Laboratory Press, 1988; Current Protocols in Immunology, Cooligan et al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff et al., Adv. in Immunol. 43: 1-98, 1988; Monoclonal Antibodies: Principles and Practice, Goding, J. W. (eds.), Academic Press Ltd., 1996; Benjamin et al., Ann. Rev. Immunol. 2: 67-101, 1984). Representative examples of such assays include: concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay.

In some embodiments, the antibodies of the present invention have at least about 1000 fold, and at least about 10,000 fold greater affinity for EphA2 than for known related family members. In some embodiments, the binding affinity of an antibody of the present invention is less than about $1\times10^5$ Ka, less than about $1\times10^4$ Ka, and preferably less than $1\times10^3$ Ka, for a related polypeptide other than EphA2.

As used herein, the term "epitope" refers to an antigenic determinant of a polypeptide. In some embodiments an epitope may comprise 3 or more amino acids in a spatial conformation which is unique to the epitope. In some embodiments epitopes are linear or conformational epitopes. Generally an epitope consists of at least 4 such amino acids, and more usually, consists of at least 8-10 such amino acids. Methods of determining the spatial conformation of amino acids are known in the art, and include, for example, x-ray crystallography and 2-dimensional nuclear magnetic resonance.

As used herein, the phrase "EphA2-related" refers to cells, samples, tumors or other pathologies that are characterized by increased evidence of EphA2 expression relative to non-cancerous and/or non-metastatic cells, samples, tumors, or other pathologies. In some preferred embodiments, EphA2-related cells, samples, tumors or other pathologies are characterized by increased evidence of EphA2 expression relative to non-metastatic cells, samples, tumors, or other pathologies.

As used herein, the phrase "homologous nucleotide sequence," or "homologous amino acid sequence," or variations thereof, refers to sequences characterized by a homology, at the nucleotide level or amino acid level, of at least a specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity.

Percent homology or identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology between the probe and target is between about 50% to about 60%. In some embodiments, nucleic acids have nucleotides that are about 60%, preferably about 70%, more preferably about 80%, more preferably about 85%, more preferably about 90%, more preferably about 92%, more preferably about 94%, more preferably about 95%, more preferably about 97%, more preferably about 98%, more preferably about 99% and most preferably about 100% homologous to SEQ ID NO:1 or SEQ ID NO:5, or a portion thereof.

Homology may also be at the polypeptide level. In some embodiments, polypeptides are about 60%, about 70%, about 80%, about 85%, about 90%, about 92%, about 94%, about 95%, about 97%, about 98%, about 99% and about 100% homologous to SEQ ID NO:2, 6, or 8, or a portion thereof.

As used herein, the term "oligonucleotide" refers to a series of linked nucleotide residues. In some embodiments oligonucleotides are used in a polymerase chain reaction (PCR). This sequence may be based on (or designed from) a genomic sequence or cDNA sequence and is used to amplify, confirm, or detect the presence of an identical, similar, or complementary DNA or RNA in a particular cell or tissue. Oligonucleotides may also be used to modulate the expression of a gene. Oligonucleotides comprise portions of a DNA sequence and have at least about 10 nucleotides and as many as about 500 nucleotides. In some embodiments oligonucleotides comprise from about 10 nucleotides to about 50 nucleotides, from about 15 nucleotides to about 30 nucleotides, and from about 20 nucleotides to about 25 nucleotides. Oligonucleotides may be chemically synthesized and can also be used as probes. In some embodiments oligonucleotides are single stranded. In some embodiments oligonucleotides comprise at least one portion which is double stranded. In some embodiments the oligonucleotides are antisense oligonucleotides (ASO). In some embodiments the oligonucleotides are RNA interference oligonucleotides (RNAi oligonucleotides).

As used herein, the term "probe" refers to nucleic acid sequences of variable length. In some embodiments probes comprise at least about 10 and as many as about 6,000 nucleotides. In some embodiments probes comprise at least 12, at least 14, at least 16, at least 18, at least 20, at least 25, at least 50 or at least 75 consecutive nucleotides. Probes are used in the detection of identical, similar, or complementary nucleic acid sequences. Longer length probes are usually obtained from natural or recombinant sources, are highly specific to the target sequence, and are much slower to hybridize to the target than are oligomers. Probes may be single- or double-stranded and are designed to have specificity in PCR, hybridization membrane-based, in situ hybridization (ISH), fluorescent in situ hybridization (FISH), or ELISA-like technologies.

As used herein, the term "in combination with" is meant to refer to administration of modulators of the invention with other therapeutic regimens. In some embodiments, the therapeutic regimens of the present invention are used with traditional treatment regimens for cancer including, without limitation, radiation therapy and/or chemotherapy, and traditional treatment regimens for diseases or disorders relating to bone, including, but not limited to, anti-resorptive agents, bisphosphonates, and the like. Administration of the modulators of the present invention may take place prior to, simultaneously with, or after traditional cancer treatment, and/or traditional bone disorder treatment.

As used herein, the term "therapeutically effective amount" is meant to refer to an amount of a medicament which produces a medicinal effect observed as reduction or reverse in one or more SREs, clinical endpoints, or metastasis of cancer cells in an individual when a therapeutically effective amount of a medicament is administered to the individual. Therapeutically effective amounts are typically determined by the effect they have compared to the effect observed when a composition which includes no active ingredient is administered to a similarly situated individual. The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein the term "isolated" refers to a polynucleotide, a polypeptide, an antibody, or a host cell that is in an environment different from that in which the polynucleotide, the polypeptide, or the antibody naturally occurs. Methods of isolating cells are well known to those skilled in the art. A polynucleotide, a polypeptide, or an antibody which is isolated is generally substantially purified.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

As used herein, the term "binding" means the physical or chemical interaction between two or more biomolecules or compounds. Binding includes ionic, non-ionic, Hydrogen bonds, Van der Waals, hydrophobic interactions, etc. Binding can be either direct or indirect, indirect being through or due to the effects of another biomolecule or compound. Direct binding refers to interactions that do not take place through or due to the effect of another molecule or compound but instead are without other substantial chemical intermediates.

As used herein, the term "contacting" means bringing together, either directly or indirectly, one molecule into physical proximity to a second molecule. The molecule can be in any number of buffers, salts, solutions, etc. "Contacting" includes, for example, placing a polynucleotide into a beaker, microtiter plate, cell culture flask, or a microarray, or the like, which contains a nucleic acid molecule. Contacting also includes, for example, placing an antibody into a beaker, microtiter plate, cell culture flask, or microarray, or the like, which contains a polypeptide. Contacting may take place in vivo, ex vivo, or in vitro.

As used herein, the phrase "stringent hybridization conditions" or "stringent conditions" refers to conditions under which a probe, primer, or oligonucleotide will hybridize to its target sequence, but to a minimal number of other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

As used herein, the term "moderate stringency conditions" refers to conditions under which a probe, primer, or oligonucleotide will hybridize to its target sequence, but to a limited number of other sequences. Moderate conditions are sequence-dependent and will be different in different circumstances. Moderate conditions are well-known to the art skilled and are described in, inter alia, Manitatis et al. (Molecular Cloning: A Laboratory Manual, Cold Spring Harbor Laboratory; 2nd Edition (December 1989)).

As used herein, the term "scfv" refers to Single Chain Antibody Variable Region Fragments. These fragments are generated from a library of antibodies, whose variable binding regions are cloned into a single polypeptide chain that retains the property of a normal antibody.

The term "region" refers to a physically contiguous portion of the primary structure of a biomolecule. In the case of proteins, a region is defined by a contiguous portion of the amino acid sequence of that protein. In some embodiments a "region" is associated with a function of the biomolecule.

The term "portion" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity.

As used herein the term "imaging agent" refers to a composition linked to an antibody, small molecule, or probe of the invention that can be detected using techniques known to the art-skilled. In some embodiments the imaging agent is, without limitation, $^{18}$F, $^{43}$K, $^{52}$Fe, $^{57}$Co, $^{67}$CU, $^{67}$Ga, $^{77}$Br, $^{87}$MSr, $^{86}$Y, $^{90}$Y, $^{99}$MTc, $^{111}$In, $^{123}$I, $^{125}$I, $^{127}$Cs, $^{129}$Cs, $^{131}$I, $^{132}$I, $^{197}$Hg, $^{203}$Pb, or $^{206}$Bi.

As used herein, the term "decoy receptor" refers to an EphA2 receptor comprising at least a portion of a polypeptide, mimetic, or other macromolecule capable of binding an EphA2 ligand. In some embodiments, the decoy receptor comprises at least a portion of an EphA2 receptor. In some embodiments the decoy receptor competes with natural EphA2 receptors for EphA2 ligands. In some embodiments, the decoy receptor is labeled to facilitate quantification, qualification, and/or visualization. In other embodiments, the decoy receptor further comprises a moiety to facilitate isolation and/or separation of the decoy receptor and or the decoy receptor-EphA2 complex. In some embodiments, the decoy receptor is a non-signaling molecule which functions by capturing EphA2 ligand and preventing it from interacting with the signaling EphA2 receptor. In some embodiments the decoy receptor comprises at least a portion of an EphA2 receptor fused to an antibody or antibody fragment.

As used herein, the term "mimetic" is used to refer to compounds which mimic the activity of a peptide. Mimetics are non-peptides but may comprise amino acids linked by non-peptide bonds. U.S. Pat. No. 5,637,677, issued on Jun. 10, 1997, and parent applications thereof, all of which are incorporated herein by reference, contain detailed guidance on the production of mimetics. Briefly, the three-dimensional structure of the peptides which specifically interacts with the three dimensional structure of the EphA2 receptor is duplicated by a molecule that is not a peptide.

The nucleic acid compositions described herein can be used, for example, to produce polypeptides, as probes for the detection of mRNA in biological samples (e.g., extracts of human cells) or cDNA produced from such samples, to generate additional copies of the polynucleotides, to generate ribozymes or oligonucleotides (single and double stranded), and as single stranded DNA probes or as triple-strand forming oligonucleotides. The probes described herein can be used to, for example, determine the presence or absence of the polynucleotides provided herein in a sample. The polypeptides can be used to generate antibodies specific for a polypeptide associated with cancer, metastases, and SREs, which antibodies are in turn useful in diagnostic methods, prognostic methods, and the like as discussed in more detail herein. Polypeptides are also useful as targets for therapeutic intervention, as discussed in more detail herein. Antibodies of the present invention may also be used, for example, to puri, detect, and target the polypeptides of the present invention, including both in vitro and in vivo diagnostic and therapeutic methods. For example, the antibodies are useful in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988). These and other uses are described in more detail below.

The present invention solves the important problem of identifying molecules involved in SREs and/or metastasis and of identifying modulators of SREs and/or metastasis. Applicants have discovered that culturing host cells with cancer cells in osteogenic media mimics what occurs in vivo when cancer metastasizes from its primary site to bone. The present invention provides long sought after models and tools for the diagnosis, detection, and treatment of SREs and metastasis as well as information about the molecular basis of cancer, SREs, and cancer metastasis.

Models of Metastasis and/or Skeletal Related Events

In some embodiments, the present invention provides models of SREs or metastasis. In some embodiments the metastasis is metastasis to bone. The models comprise co-culturing host cells and cancer cells. In some embodiments, the host cells and/or cancer cells are isolated host and/or cancer cells. In some embodiments, the host cells are derived from bone marrow, bone, blood, placenta, and umbilical cord. In some preferred embodiments, the host cells are mesenchymal stem cells.

Biological markers on said co-cultured cells and the effect of modulating compositions and certain variables can be assessed using the model by comparison to controls. In some embodiments, the control cancer cell is isolated from the same initial cancer cell culture as was the cancer cell used in the co-culture. In some embodiments, the biological marker is the presence or absence of evidence of EphA2 expression.

In some embodiments, the cancer cells and host cells are co-cultured in osteogenic media. In some embodiments, the osteogenic media comprises Mesenchymal Stem Cell Growth Medium ("MSCGM") and bullet kit growth supplements, (catalogue #: PT-3001; Biowhittaker™). In some embodiments, the media further comprises from about $10^{-8}$M dexamethasone, from about $10^{-7}$M dexamethasone to about $10^{-2}$M dexamethasone or at least 107 M dexamethasone.

In some embodiments, the osteogenic media comprises from about 0.001 mM to about 1000 mM ascorbate acid, about from about 0.05 mM to about 100 mM ascorbate acid, from about 0.05 mM to about 50 mM ascorbate acid, from about 0.05 mM to about 25 mM ascorbate acid. In some embodiments the media comprises about 0.05 mM ascorbate acid.

In some embodiments, the media comprises from about 0.1 mM to about 1000 mM betaglycerophosphate, from about 1 mM to about 500 mM betaglycerophosphate, from about 5 mM to about 250 mM betaglycerophosphate, and from about 10 mM to about 50 mM betaglycerophosphate. In some embodiments, the media comprises about 10 mM betaglycerophosphate.

In some embodiments of the present invention, the media comprises about $10^{-7}$M dexamethasone, about 0.05 mM ascorbate phosphate, and about 10 mM betaglycerophosphate.

In some embodiments the model is an in vitro model. In some embodiments the model is a xenograft model.

Methods of Determining Functions of Genes in SREs or Metastasis

The present invention also provides methods for determining the function or effect of various genes on SREs or on the metastasis of cancer cells to bone. In some embodiments the method comprises co-culturing one or more cancer cells with one or more host cells and comparing one or more biological markers on said cancer and/or host cells to the same biological markers on cancer and/or host cells not co-cultured. In some embodiments, the control cancer cell is isolated from the same initial cancer cell culture as was the cancer cell used in the co-culture.

Methods of Identifying Markers of SREs or Metastasis

The present invention also provides methods of identifying biological markers of SREs and/or metastasis. In some embodiments, the biological markers that are identified include, without limitation, genes, gene products, RNA, mRNA, DNA, and the like. The method comprises co-culturing host cells and cancer cells and detecting evidence of modulation.

In some embodiments, evidence of modulation is detected by comparing expression profiles of co-cultured host and cancer cells to expression profiles of host and/or cancer cells not co-cultured.

In some embodiments, the biological marker is evidence of expression of EphA2.

Methods of Identifying Modulators of SREs or Metastasis

The present invention provides methods for identifying modulators of SREs or metastasis. In some embodiments, the method comprises contacting a putative modulator to the co-culture of cells.

In some embodiments, the putative modulator is incubated with the co-culture for about 1 to about 20 days. In some embodiments, the putative modulator is incubated with the co-culture for about 5 to about 14 days. In some embodiments, the putative modulator is incubated with the co-culture for about 10 to about 15 days. In some embodiments, the putative modulator is incubated with the co-culture for about 11 to about 14 days.

In some embodiments, the putative modulator is contacted to the co-culture at two or more concentrations. In some embodiments, the modulator is added to a final concentration of at least about 1 nM, at least about 100 nM, at least about 1

μM, at least about 100 μM, at least about 1 mM, at least about 100 mM, at least about 1 M, at least about 5 M, and at least about 10 M.

In some embodiments, biological markers on co-cultured cancer and host cells are compared to biological markers on co-cultured cancer cells and host cells in the absence of a putative modulatory compound. Putative modulatory compounds that decrease the quality or quantity of biological markers indicative of SREs or metastasis are thereby identified as inhibitors of SREs or metastasis.

In some embodiments, putative modulators of SREs or metastasis are compared in a mouse xenograft model in which human tissues are implanted in the subject mouse. An example of a suitable model is set forth in Nemeth et al., Cancer Research 59, 1987-1993, Apr. 15, 1999, which is incorporated by reference in its entirety. Biological markers, SREs, or clinical endpoints are determined and measured in control mice (without putative modulators) and in test mice (with putative modulators). Those skilled in the art are credited with the ability to determine criteria of the screen including without limitation, dosages, duration of treatment, relevant sample size, and the like.

Methods of Testing the Effect of Variables on SREs or Metastasis

The present invention further provides methods for testing the effect of different variables on the development of SREs or metastases. Variables tested may include the effect of the presence or absence of one or more hormones, growth factors, and nutrients. The methods comprise contacting a biomolecule with a co-culture of cancer cells and host cells. Biological markers are compared to biological markers on co-cultured cancer cells and host cells in control cells with a differing amount of the variable. In some embodiments, the control cells are cultured in the absence of the variable. Variables that decrease the quality or quantity of biological markers indicative of SREs and/or bone metastasis are thereby identified as inhibitors of SREs and/or bone metastasis.

Methods of Determining Appropriateness of Treatment Regimens

The present invention further provides methods to determine whether or not a patient is susceptible to an SRE or a metastasis and whether a particular treatment regimen is appropriate. The methods comprise co-culturing cancer cells from a patient or patient sample with host cells, and comparing biological markers from said co-cultured host and cancer cells with biological markers from control cancer cells and/or host cells not co-cultured.

In some embodiments, the control cancer are negative controls and are not of a lineage that is likely to lead to one or more SREs or metastasize to bone. In other embodiments the control cancer cells are positive controls and are of a lineage that are likely to lead to one or more SREs or metastasize to bone. Those of skill in the art can readily determine whether biological markers of a co-cultured cancer cell and host cell correlate most closely with a negative control, indicating that SRE or bone metastasis is not likely in the patient, or if the biological markers correlate most closely with a positive control, indicating that SRE or metastasis is possible in the patient.

Methods of Identifying Molecules Present on Metastatic Cancer Cells

The present invention also provides methods for identifying molecules present on cancer cells during metastasis to bone or on cancer cells destined to be metastatic or lead to SREs. In some embodiments the molecules are on the surface of the cancer cell. In some embodiments, the method comprises co-culturing cancer cells and host cells. The co-culture is then treated with phage that express scfvs. The phage are added to the media under conditions such that the scfv's can bind to the co-cultured cells. After allowing the phage to bind, cells bound to phage are isolated. Phage isolation techniques are well known to the art-skilled and include, without limitation, flow cytometry, immunopurification, gradient purification, centrifugation, and the like. After isolating the scfv's that bound to the co-cultured cells, the scfv's are sequenced and characterized. The scfv is then used to identify the antigen binding partner that was present on the cell. Methods of identifying antigen binding partners based on bound scfvs are well-known to those skilled in the art.

In some embodiments the scfv is Scfv7. In some embodiments, the antigen binding partner is EphA2.

Methods of Inhibiting SREs or Metastasis

In some embodiments the present invention provides methods of inhibiting SREs or metastasis in a patient comprising administering a therapeutically effective amount of the modulators of the present invention described supra and infra. In some embodiments the modulators were identified in accordance with the methods of the present invention.

A therapeutically effective amount of the modulating compound can be determined empirically, according to procedures well known to medicinal chemists, and will depend, inter alia, on the age of the patient, severity of the condition, and on the ultimate pharmaceutical formulation desired. Methods of administration of compositions for use in the invention include, but are not limited to, intradermal, intramuscular, intraperitoneal, intravenous, subcutaneous, intraocular, oral and intranasal. Other suitable methods of introduction can also include rechargeable or biodegradable devices and slow or sustained release polymeric devices. As discussed above, the therapeutic compositions of this invention can also be administered as part of a combinatorial therapy with other known anti-cancer agents or other known anti-bone disease treatment regimen.

In some embodiments, expression profiles and/or biological markers of the co-cultured cancer and host cells in the presence of the putative modulator compound are compared to expression profiles and/or biological markers of the cancer and host cells in the absence of the putative modulator compound. In some embodiments, the putative modulator compound inhibits one or more SREs and/or metastasis. In some embodiments, the biological marker is EphA2.

In some embodiments, the present invention provides methods of modulating SREs or metastasis comprising administering a therapeutically effective amount of an EphA2 inhibitor to a patient. In some embodiments, the cancer is prostate or breast cancer and the metastasis is a bone metastasis.

In some embodiments, the EphA2 modulator is an oligonucleotide. In some embodiments the oligonucleotide is an antisense or RNAi oligonucleotide. In some embodiments the oligonucleotide is complementary to a region, domain, portion, or segment of a gene correlated with metastasis or a SRE. In some embodiments, the gene is complementary to a region, domain, portion, or segment of EphA2. In some embodiments, the oligonucleotide comprises from about 5 to about 100 nucleotides, from about 10 to about 50 nucleotides, from about 12 to about 35, and from about 18 to about 25 nucleotides. In some embodiments, the oligonucleotide is at least 50%, at least 60%, at least 70%, at least 80%, at least 90%, at least 95%, at least 96%, at least 97%, at least 98%, at least 99%, or at least 100% homologous to a region, portion, domain, or segment of the EphA2 gene. In some embodiments there is substantial sequence homology over at least 15, 20, 25, 30, 35, 40, 50, or 100 nucleotides of the EphA2 gene.

In some embodiments there is substantial sequence homology over the entire length of the EphA2 gene. In some embodiments, the oligonucleotide binds under moderate or stringent hybridization conditions to a nucleic acid molecule having a nucleotide sequence of SEQ ID NO:1 or 5. In some embodiments, the oligonucleotide has a nucleotide sequence selected from the group consisting of SEQ ID NO:3, SEQ ID NO:72, SEQ ID NO:73, SEQ ID NO:74, SEQ ID NO:75, SEQ ID NO:76, SEQ ID NO:77, SEQ ID NO:78, SEQ ID NO:79 or SEQ ID NO:80.

In some embodiments, the EphA2 modulator is a double stranded RNA (dsRNA) molecule and works via RNAi (RNA interference). In some embodiments, one strand of the dsRNA is at least 50%, at least 60%, at least 70%, at least 80%, at least 90%, at least 95%, at least 96%, at least 97%, at least 98%, at least 99%, or at least 100% homologous to a region, portion, domain, or segment of the EphA2 gene. In some embodiments there is substantial sequence homology over at least 15, 20, 25, 30, 35, 40, 50, 100, 200, 300, 400, 500, or 1000 nucleotides of the EphA2 gene. In some embodiments there is substantial sequence homology over the entire length of the EphA2 gene.

In some embodiments the EphA2 modulator is an antibody. In some embodiments the antibody is specific to the N-terminus of the gene product of the gene associated with metastasis and/or SRE. In other embodiments, the antibody is specific to the C-terminus of the gene associated with metastasis and/or SRE. In some embodiments, the antibody is specific to a region, domain, portion, or segment of the gene associated with metastasis and/or SRE that is between the N- and C-termini of the protein. In some embodiments, the antibody is specific to a region that spans both the N-terminus and the region that is between the N- and C-termini. In other embodiments, the antibody is specific for a region that spans both the C-terminus and the region that is in between the N- and C-termini. In some embodiments, the gene is EphA2. In some embodiments the antibody binds to an epitope of a polypeptide having an amino acid sequence of SEQ ID NO:2, 6, or 8. In some embodiments the antibody binds to an epitope having an amino acid sequence of SEQ ID NOs: 12-71.

In some embodiments the binding affinity of EphA2 antibodies for EphA2 is at least $1\times10^6$ Ka. In some embodiments the binding affinity of EphA2 antibodies for EphA2 is at least $5\times10^6$ Ka, at least $1\times10^7$ Ka, at least $2\times10^7$ Ka, at least $1\times10^8$ Ka, or greater. Antibodies of the present invention may also be described or specified in terms of their binding affinity to a polypeptide of the invention. In some embodiments binding affinities include those with a Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M, or less.

The invention also provides antibodies that competitively inhibit binding of an antibody to an epitope of the invention as determined by any method known in the art for determining competitive binding using, for example, immunoassays. In some embodiments, the antibody competitively inhibits binding to the epitope by at least 95%, at least 90%, at least 85%, at least 80%, at least 75%, at least 70%, at least 60%, or at least 50%.

In some embodiments, the EphA2 antibody is specific for an epitope of EphA2 selected from the group set forth below. In some embodiments the EphA2 antibody is specific for an epitope of the extracellular region of EphA2 (SEQ ID NO:8, residues 1-535 of SEQ ID NO:2). It is to be understood that these peptides do not necessarily precisely map one epitope, but may also contain EphA2 sequence that is not immunogenic. The following sequences are given by amino acid number (i.e., "AAn") where n is the amino acid number of the amino acid sequence set forth in SEQ ID NO:2 or 8. For example, in the context of "AA80-AA90", an epitope is defined from about amino acid 80 of SEQ ID NO:2 or 8 to about amino acid 90 of SEQ ID NO:2. In the context of epitopes, the term "about" refers to +/−one or two amino acid residues:

AA1-AA25; AA1-AA50; AA1-AA84; AA9-AA177; AA1-AA10; AA5-AA20; AA20-AA25; AA35-AA45; AA48-AA52; AA50-AA100; AA40-AA90; AA45-AA65; AA65-AA75; AA80-AA90; AA88-AA92; AA99-AA120; AA95-AA110; AA105-AA120; AA100-AA150; AA132-AA137; AA150-AA200; AA155-AA170, AA190-AA210; AA198-AA202; AA200-AA250; AA220-AA240; AA238-AA234; AA245-AA265; AA250-AA300; AA290-AA330; AA290-305; AA300-AA350; AA3310-AA330; AA3317-AA322; AA348-AA352; AA350-AA400; AA380-AA395; AA382-AA387; AA405-AA495; AA400-AA450; AA405-AA415; AA415-AA425; AA425-AA435; AA437-AA582; AA450-AA500; AA440-AA460; AA446-AA440; AA460-AA470; AA460-AA464; AA472-AA478; AA475-AA495; AA500-AA550; AA511-AA690; AA515-AA550; AA550-AA600; AA550-AA625; AA575-AA605; AA585-AA600; AA600-AA650; AA600-AA625; AA635-AA665; AA650-AA700; AA645-AA680; AA700-AA750; AA700-AA725; AA700-AA750; AA725-AA775; AA770-AA790; AA750-AA800; AA800-AA815; AA825-AA850; AA850-AA875; AA800-AA850; AA920-AA990; AA850-AA900; AA920-AA945; AA940-AA965; AA970-end (C' terminal).

Methods of predicting other potential epitopes to which an antibody of the invention can bind are well-known to those of skill in the art and include without limitation, Kyte-Doolittle Analysis (Kyte, J. and Dolittle, R. F., J. Mol. Biol. (1982) 157:105-132), Hopp and Woods Analysis (Hopp, T. P. and Woods, K. R., Proc. Natl. Acad. Sci. USA (1981) 78:3824-3828; Hopp, T. J. and Woods, K. R., Mol. Immunol. (1983) 20:483-489; Hopp, T. J., J. Immunol. Methods (1986) 88:1-18), Jameson-Wolf Analysis (Jameson, B. A. and Wolf, H., Comput. Appl. Biosci. (1988) 4:181-186), and Emini Analysis (Emini, E. A., Schlief, W. A., Colonno, R. J. and Wimmer, E., Virology (1985) 140:13-20).

In some embodiments the antibody is selected from the group consisting of a monoclonal antibody, a humanized antibody, a chimeric antibody, a primatized antibody, a phage-displayed antibody, a single chain antibody, or a fragment of any of the preceding. In some preferred embodiments the antibody is a humanized antibody.

Antibodies of the present invention may function through different mechanisms. In some embodiments, antibodies trigger antibody-dependent cellular cytotoxicity (ADCC), a lytic attack on antibody-targeted cells. In some embodiments, antibodies have multiple therapeutic functions, including, for example, antigen-binding, induction of apoptosis, and complement-dependent cellular cytotoxicity (CDC)

Antibodies of the present invention may act as agonists or antagonists of the polypeptides of the present invention. For example, in some embodiments the present invention provides antibodies which disrupt the receptor/ligand interactions with the polypeptides of the invention either partially or fully. In some embodiments antibodies of the present invention bind an epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques known in the art. For example, receptor activation can be determined by detecting the phosphorylation (e.g., tyrosine or serine/threonine) of the receptor or its substrate by immunoprecipitation followed by Western blot analysis. In some embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The present invention further provides receptor-specific antibodies which both prevent ligand binding and receptor activation as well as antibodies that recognize the receptor-ligand complex, and, in some embodiments, do not specifically recognize the unbound receptor or the unbound ligand.

In some embodiments neutralizing antibodies are provided which bind the ligand and prevent binding of the ligand to the receptor, as well as antibodies which bind the ligand, thereby preventing receptor activation, but do not prevent the ligand from binding the receptor.

In some embodiments the present invention provides activating antibodies. These antibodies may act as receptor agonists, i.e., modulating either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. Antibody agonists can be made using methods known in the art. See, e.g., PCT publication WO 96/40281; U.S. Pat. No. 5,811,097; Deng et al., Blood 92(6): 1981-1988 (1998); Chen et al., Cancer Res. 58(16): 3668-3678 (1998); Harrop et al., J. Immunol. 161(4): 1786-1794 (1998); Zhu et al., Cancer Res. 58(15): 3209-3214 (1998): Yoon et al., J. Immunol. 160(7):3170-3179 (1998); Prat et al., J. Cell. Sci. 111(Pt2): 237-247 (1998); Pitard et al., J. Immunol. Methods 205(2): 177-190 (1997); Liautard et al., Cytokine 9(4): 233-241 (1997); Carlson et al., J. Biol. Chem. 272(17): 11295-11301 (1997); Taryman et al., Neuron 14(4):755-762 (1995); Muller et al., Structure 6(9): 1153-1167 (1998); Bartunek et al., Cytokine 8(1):14-20 (1996).

As discussed in further detail supra and infra, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Suitable antibodies according to the present invention can recognize linear or conformational epitopes, or combinations thereof. Antibodies useful in the present invention are described, for example, Examples of antibodies useful in the present invention are set forth, inter alia, in U.S. patent application Ser. No. 10/436,782, WO 01/12172, WO 01/12840 and WO/2004014292, each which is herein incorporated by reference in its entirety.

The present invention also provides antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include, without limitation, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholincsterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, or $^{99}$Tc.

In some embodiments the antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples of cytotoxins or cytocidals include one or more of paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Antibody conjugates of the present invention can be used for modifying a given biological response. For example, in some embodiments the drug moiety may be a protein or polypeptide, or fragments thereof, possessing a desired biological activity. Such proteins include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al. Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies of the present invention may also be attached to solid supports, which are particularly useful for immunoassays or purification of the target antigen. Such solid supports include without limitation, glass, cellulose, polyacrylamide, nylon, polystyrene, polyvinyl chloride or polypropylene.

Techniques for conjugating such therapeutic moieties to antibodies are well known to the art skilled, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

In some embodiments the antibodies of the present invention can be conjugated to a second antibody to form an antibody heteroconjugate (see, for example U.S. Pat. No. 4,676,980).

In some embodiments the present invention provides therapeutic antibodies, with or without a therapeutic moiety conjugated thereto, administered alone or in combination with other agents, including, for example, cytotoxic factor(s) and/or cytokine(s).

In some embodiments, the antibody disrupts or prevents cell-cell interactions. In some preferred embodiments the cell-cell interaction is between a host cell and a cancer cell.

In some embodiments, the antibody competes with Scfv7 for binding to an epitope of EphA2. In some preferred embodiments, the epitope of EphA2 is present on the surface of a cancer or host cell.

In some embodiments, the EphA2 modulator is a small molecule. In some embodiments, the small molecule has a molecular weight that is less than about 9, about 8, about 7, about 6, about 5, about 4, about 3, about 2, about 1 kilodaltons.

The present invention also provides methods to prophylactically treat a patient who is predisposed to develop one or more SREs or a metastasis to bone or who has had a SRE or metastasis to bone and is therefore susceptible to a relapse or recurrence. The methods are particularly useful in high-risk individuals who, for example, have a family history of SREs or metastasizing tumors, or show a genetic predisposition. In some embodiments the tumors are EphA2-related tumors. Additionally, the methods are useful to prevent patients from having recurrences of EphA2-related tumors who have had EphA2-related tumors removed by surgical resection.

Methods of treatment comprise administering single or multiple doses of antibodies, small molecules, mimetics, decoy receptors, or oligonucleotides, or combinations and subcombinations of the above. In some embodiments the antibodies, small molecules, mimetics, decoy receptors, or oligonucleotides are administered as injectable pharmaceutical compositions that are sterile, pyrogen free and comprise the antibodies, small molecules, decoy receptors, mimetics or oligonucleotides in combination with a pharmaceutically acceptable carrier or diluent.

According to some aspects, the patient in need of anti-cancer treatment is treated with the antibodies, small molecules, mimetics, decoy receptors, or oligonucleotides in conjunction with chemotherapy and/or radiation therapy. For example, following administration of the antibodies, small molecules, mimetics, decoy receptors, or oligonucleotides, the patient may also be treated with a therapeutically effective amount of anti-cancer radiation. In some embodiments chemotherapeutic treatment is provided in combination with the antibodies, small molecules, mimetics, decoy receptors, or oligonucleotides. In some embodiments antibodies, small molecules, mimetics, decoy receptors, or oligonucleotides are administered in combination with chemotherapy and radiation therapy.

In some embodiments, two or more of antibodies, small molecules, mimetics, decoy receptors, or oligonucleotides are administered to the patient.

Methods of Inhibiting Cancer Cell Migration and/or Adhesion

In some embodiments the present invention provides methods of inhibiting cancer cell migration or adhesion comprising administering a therapeutically effective amount of the modulators of the present invention described supra and infra. In some embodiments the modulators were identified in accordance with the methods of the present invention.

In some embodiments the methods are performed in vivo, or in vitro. In some embodiments the cancer cells are selected from the group consisting of breast, prostate, colon, and melanoma cells.

Pharmaceutical Compositions

The present invention also provides pharmaceutical compositions comprising one or more of the modulators described herein and a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

In some embodiments the pharmaceutical compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington: The Science and Practice of Pharmacy* (1995) Alfonso Gennaro, Lippincott, Williams, & Wilkins.

Methods of Detecting Metastases

The present invention also provides methods for detecting metastases in a patient. In some embodiments the method comprises administering a composition to the patient comprising antibodies, probes, and small molecules linked to an imaging agent and detecting the localization of the imaging agent in the patient. In some embodiments, an anti-EphA2 antibody conjugated to an imaging agent is administered to the patient to detect one or more metastases. The labeled antibodies will bind to the high density of receptors on cells and thereby accumulate on the tumor cells. Using standard imaging techniques, the site of the tumors can be detected.

In some embodiments the imaging composition is administered to the body of the patient. In some embodiments, the imaging composition is contacted to a sample obtained from the patient.

The present invention is also useful as providing methods to quantify the amount of a gene product of interest present in a patient, cell or sample. The methods comprise administering labeled antibodies, probes, and small molecules to a patient or sample and detecting the amount of gene product present in the sample. Such information indicates whether or not a tumor is related to the gene, and, therefore, whether specific treatments should be used or avoided. In some embodiments, using standard techniques well known to the art-skilled, samples believed to include tumor cells are obtained and contacted with labeled antibodies, probes, oligonucleotides, and small molecules. After removing any unbound, labeled antibodies, probes, oligonucleotides or small molecules, the quantity of labeled antibodies, peptides, oligonucleotides or mimetics bound to the cell, or the quantity of antibodies, peptides, oligonucleotides or mimetics removed as unbound is determined. The information directly relates to the amount of gene product present. In some embodiments the gene is EphA2.

Imaging can be performed using procedures well known to those of ordinary skill in the art. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as an iron chelate. MRI scanning may employ chelates of gadolinium or manganese. Additionally, positron emission tomography (PET) may be possible using positron emitters of oxygen, nitrogen, iron, carbon, or gallium.

Methods of Detecting SREs and/or Clinical Endpoints

The present invention also provides methods for detecting SREs and/or clinical endpoints in a patient. In some embodiments the method comprises administering a composition to the patient comprising antibodies, probes, and small molecules linked to an imaging agent and detecting the localization of the imaging agent in the patient. In some embodiments, an anti-EphA2 antibody conjugated to an imaging agent is administered to the patient to detect one or more metastases. The labeled antibodies will bind to the high density of receptors on cells and thereby accumulate on the tumor cells. Using standard imaging techniques SREs and parameters relating to clinical endpoints can be detected and/or assessed.

In some embodiments the imaging composition is administered to the body of the patient. In some embodiments, the imaging composition is contacted to a sample obtained from the patient.

Imaging can be performed using procedures well known to those of ordinary skill in the art. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as an iron chelate. MRI scanning may employ chelates of gadolinium or manganese. Additionally, positron emission tomography (PET) may be possible using positron emitters of oxygen, nitrogen, iron, carbon, or gallium.

Therapeutic Regimens

In some embodiments, the present invention provides methods of modulating metastasis or SREs comprising first identifying patient susceptible to EphA2 therapy comprising the steps of administering to the patient in need thereof a composition comprising an antibody, probe, primer, or oligonucleotide linked to an imaging agent and detecting the presence or absence of evidence of the gene or gene product in the patient. In some embodiments the gene is EphA2. The presence of evidence of EphA2 expression in the patient is indicative of a patient who is a candidate for EphA2 therapy and the absence of evidence of EphA2 expression in the patient is indicative of a patient who is not a candidate for EphA2 therapy. In some embodiments a patient susceptible to EphA2 therapy is identified comprising the steps of administering to the patient a composition comprising an EphA2 oligonucleotide or antibody linked to an imaging agent and detecting the presence or absence of clinical endpoints indicative of a SRE or metastasis in the patient. The presence of clinical endpoints indicative of a SRE or metastasis is indicative of a patient who is a candidate for EphA2 therapy and the absence of evidence of clinical endpoints indicative of a SRE or metastasis is indicative of a patient who is not a candidate for EphA2 therapy.

In some embodiments, the present invention further provides administering one or more EphA2 modulators to the patient if the patient is a candidate for EphA2 therapy and treating the patient with conventional cancer treatment if the patient is not a candidate for EphA2 therapy.

In some embodiments the clinical endpoint is selected from the group consisting of fractures, spinal cord compression, and hypercalcemia. In some embodiments clinical endpoints are detected radiologically.

Kits

In some embodiments, the present invention provides kits for imaging and/or detecting a gene or gene product correlated with SREs and/or metastases. In some embodiments the gene is EphA2. Kits of the invention comprise detectable antibodies, small molecules, oligonucleotides, decoy receptors, mimetics or probes as well as instructions for performing the methods of the invention. Optionally, kits may also contain one or more of the following: controls (positive and/or negative), containers for controls, photographs or depictions of representative examples of positive and/or negative results.

Each of the patents, patent applications, Genbank accession numbers and publications described herein is hereby incorporated by reference in its entirety.

Various modifications of the invention, in addition to those described herein, will be apparent to those of skill in the art in view of the foregoing description. Such modifications are also intended to fall within the scope of the appended claims. The present invention is further demonstrated in the following examples that are for purposes of illustration and are not intended to limit the scope of the present invention.

EXAMPLES

Example 1

Co-Culture of Host Cells and Cancer Cells

One vial (750,000 cells/vial) of normal human mesenchymal stem cells (MSC, catalogue #:PT-2501 from BioWhittaker™) were plated in osteogenic media comprising complete MSCGM with $10^{-7}$M dexamethasone, 0.05 mM ascorbate phosphate, 10 mM betaglycerophosphate and allowed to attach to the cell culture plate overnight. The stem cells were plated at a density of 10,000 cells/cm$^2$. The next day subconfluent cancer cells were trypsinized and resuspended in osteogenic media for counting. The cancer cells were diluted to 40,000 cells/ml in osteogenic media. The media from the MSC cells was removed and the cancer cells were added at the same density, as the stem cells were the previous day (10,000 cells/cm$^2$).

Example 2

Detection of Biological Markers

Alkaline Phosphatase Staining

Media was removed from the cultured cells. The cells were fixed for 3-5 minutes with 10% neutral buffered formalin. After 3-5 minutes the formalin was removed and replaced with phosphate buffered saline (PBS). The PBS was then replaced with alkaline phosphatase stain. Alkaline phosphatase stain was prepared by adding one capsule (12 mg) of Fast Blue RR (Sigma™, catalogue #FBS-25) to 48 ml of water. After mixing the solution, the solution was filtered. To the filtered solution 2 ml of Naphthol AS-MX phosphate (Sigma™, catalogue #: 85-5) was added. The stain was allowed to incubate for about 30 minutes at 37° C. and then was rinsed with PBS. Alkaline Phosphatase stain was then visualized under a microscope.

Endpoint Alkaline Phosphatase Assay

The cell layer was washed with PBS (w/o Mg and Ca). 100 μl of cell digestion buffer (1:10 dilution of assay buffer [1.5 M Tris pH 9.0, 1 mM $ZnCl_2$, 1 mM $MgCl_2$]+1% Triton X-100™) was added to each well of a 96 well plate. The digestion buffer was incubated for about 30 minutes at 37° C. The lysates were then transferred to a fresh 96-well plate. To a new 96-well plate, 50 μl substrate (1 capsule Sigma™ 104 in 10 ml $H_2O$), 50 μl alkaline phosphatase buffer (1.5 M Tris pH 9.0, 1 mM $ZnCl_2$, 1 mM $MgCl_2$) and 10 μl cell lysate was added. The mixture was incubated for 15 minutes at 37° C. The reaction was stopped by the addition of 100 μl NaOH. The O.D. was then read at 410 nm.

Von Kossa Stain (for the Visualization of Calcium Deposits)

The cells were fixed for 5 minutes with 10% neutral buffered formalin. After 5 minutes, the fixative was removed and the cells rinsed with deionized water. To the cells a 5% aqueous silver nitrate solution was added. The cells were then exposed to ultraviolet light for 1 hour with the lid of the cell culture dish removed. The reaction was stopped with the addition of 5% aqueous sodium thiosulfate for 2-3 minutes at room temperature. Cells were then washed and stored at room temperature.

Example 3

Analyzing Bone Metastasis

Mesenchymal stem cells were plated in a 96-well dish at a density of 10,000 cells/cm$^2$ in osteogenic media and allowed to attach overnight at 37° C. At the same time cancer cells (PC3, LNCaP, or MDA231) were plated subconfluent. The next day, the cancer cells were trypsinized and resuspended in osteogenic media at a concentration of 40,000 cells/ml. The media was then removed from the 96-well plate containing the host cells. The cancer cells were then added to the host cell culture at a density of 10,000 cells/cm$^2$. Alkaline phosphatase activity was measured on day 4. Calcium deposits were analyzed by incubating cells for 11-14 days changing the media every 2-3 days. The calcium deposits were visualized using the Van Kossa Stain on days 11-14.

Example 4

Prostate Cancer Cells Stimulate MSC to Become Osteoblasts

Mesenchymal stem cells (MSC) were cultured alone or in the presence of PC3 (prostate cancer cells) or MDA231 (breast cancer cells) for four days in osteogenic media. On the fourth day the cells were fixed and stained for alkaline phosphatase activity. (FIGS. 1 and 2). As can be seen in FIG. 1, only in the presence of PC3 cells were host cells stimulated to become osteoblasts, which is indicated by the presence of the dark stain. Alkaline phosphatase activity was also measured by creating cell lysates. As can be seen in FIG. 2 the alkaline phosphatase activity is significantly greater in the presence of the PC3 cells than when the cells are absent.

Figure 3:
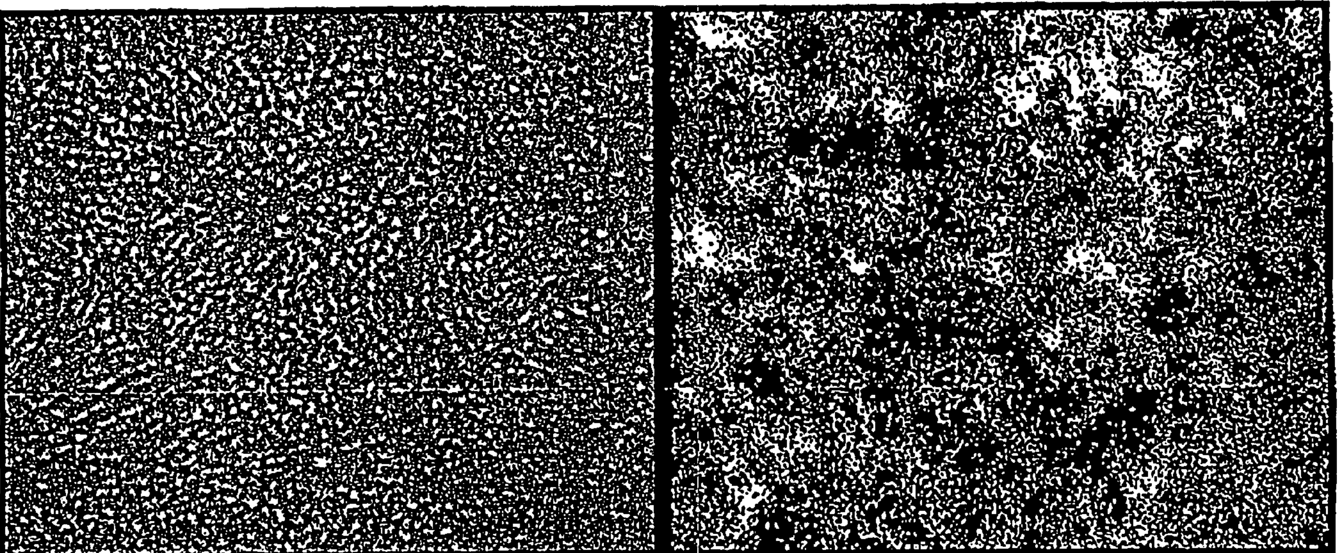
FIG. 3 depicts Van Kossa staining, 13 days after co-culture. The left panel depicts Von Kossa staining of mesenchymal stem cells cultured alone. The right panel depicts Von Kossa staining of the MSC and LNCAP when co-cultured. The staining of the co-culture is more than the culture of the stem cells alone and is indicative of bone metastasis and an osteoblastic response to bone metastasis.
Figure 10:
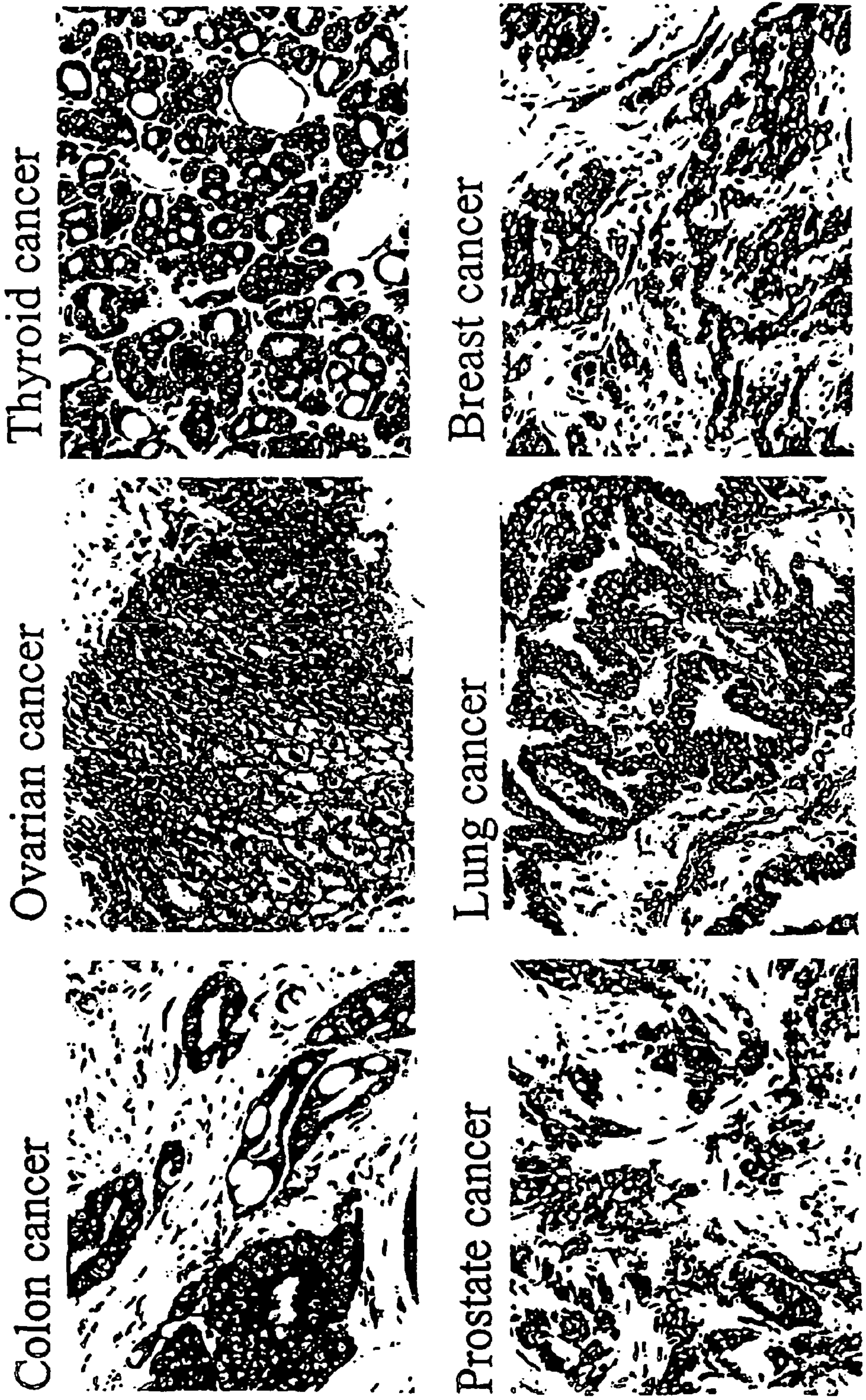
FIG. 10 depicts the expression of EphA2 in several cancer types.

Mesenchymal stem cells were co-cultured with LNCaP (prostate cancer cells) for 13 days in osteogenic media. On day 13 the cells were fixed and stained for calcium phosphate (FIG. 3). As can be seen in FIG. 3, the LNCAP cells stimulated the calcium deposits indicating that the host cells have begun differentiating into an osteoblast.

Example 5

Gene Expression Analysis

To identify genes whose expression is modulated during bone metastasis, the following procedure was performed. Mesenchymal stem cells were cultured alone or in the presence of PC3 cells for 4 or 11 days in osteogenic media. At the appropriate time total RNA was isolated from the cells. RNA was subjected to reverse transcription and analyzed for the expression of specific genes with the Roche Light Cycler™. As can be seen in FIG. 4, the expression of the alkaline phosphatase gene, osteocalcin, and CBFA2 RNA increased during bone metastasis. The expression of the negative controls, NC1 and NC2, was not increased during bone metastasis.

Example 6

Identification of a Cell Surface Molecule

For phage selection on co-culture, a fresh culture of the TG1 *E. coli* host strain was grown to an optical density at 600 nm ($OD_{600}$) of 0.8 in Luria Broth with 1% glucose.

For biopanning, co-culture cells, MSC and cancer cells, or cells to be panned on, or cultured cells were grown in 6-well dishes and washed twice with Dulbecco's Phosphate Buffered Saline (dPBS). Adherent cells were blocked with 5% MPBS (5% Marvel milk powder in PBS) for 45 min at 37° C. For each 6-well dish to be screened, 100 μl ($10^{11}$ colony forming units (cfu) of the phage display library) was blocked in 800 μl 5% MPBS, reserving a 100 μl aliquot of this blocked phage for determination of the input titre. Blocked cells were washed twice with dPBS, and then phage were incubated with cells for 2 hours on ice. The phage-treated cells were then rinsed 3 times with PBST (PBS containing 0.05% Tween20™), washed twice for 5 min. with PBST on a shaker at 4° C., and then washed three times with PBS. Bound phage in each well were eluted with 400 μl 0.1 M glycine pH 2.2 for 15 min. at ambient temperature, and the elution reaction was stopped using 80 μl 1.5M Tris pH 8.8.

For amplification of selected phage, 4.5 ml of the freshly grown TG1 culture was added directly to each well containing eluted phage. TG1 bacteria were incubated for 45 min at 37° C. without shaking, and a 200 μl aliquot of the phage-infected TG1 was saved for determination of the output titre. For the last round of screening, an aliquot was also saved in 2×YT broth containing 15% glycerol at −80° C. Infected bacteria were then incubated for 1 hr at 37° C. with shaking (250 rpm). Phage supernatant was drawn off and diluted 5-fold (to 25 ml) with healing media (2×YT with Chloramphenicol, 34 μg/ml (Cm34), 1% Glucose), and the $OD_{600}$ of 50 μl was determined using a plastic cuvette. The phage-infected TG1 culture was grown at 37° C. until the $OD_{600}$ reached approximately 0.5.

For superinfection and phage packaging, 50 μl of VCSM13 helper phage (kanamycin resistant ($kan^r$)) was added for every 5 ml of culture at $OD_{600}$=0.5, for a multiplicity of infection (m.o.i.) of 20. Helper phage were allowed to infect by incubation at 37° C. for 30 min without shaking and then grown for 30 min with shaking. Super-infected TG1 were centrifuged at 4° C. at 4500×g for 5 min, and then washed with 25 ml induction media [2×YT with Cm34, Kan50 (kanamycin 50 μg/ml), and 0.1 mM IPTG]. Bacteria were then resuspended in 50 ml induction media and incubated overnight at 30° C. with shaking. After overnight induction, the culture was centrifuged for 10 min at 10,000×g at 4° C. and to the cleared supernatant fraction, 10 ml of 20% PEG, 2.5 M NaCl was added, mixed well and held on ice for 30 min. The PEG precipitated phage were centrifuged for 30 min at 10,000×g at 4° C., and the pellet resuspended in 5 ml PBS. Remaining bacterial debris were pelleted at maximum G-force in a tabletop microcentrifuge for 1 min at ambient temperature. The cleared supernatant was passed through a 0.45 μM10.22 μM sterile filter, and 200 μl was saved for determining titre of input phage for next steps. To remaining purified phage, sterile glycerol was added to a final concentration of 15%, and this stock was stored at −80° C.

For purification of DNA from the phagemid, 5 ml of infected TG1 bacteria were used to inoculate 100 ml 2×YT broth containing Cm34 and culture was grown overnight at 37° C. DNA was prepared from phagemids using the Qiagen midi or maxiprep kit according to the manufacturer's directions.

Colonies were picked for sequencing of selected phagemids, 1 ml overnight cultures were prepared in 2×YT, chloramphenicol, 1% glucose.

For competitive biopanning using GFP and 2nd round subcloning, a fresh culture of the TG1 strain was grown to an $OD_{600}$ of 0.8 in 100 ml LB, 1% glucose. In one 6-well dish, co-cultures with unlabeled hMSC and GFP-labeled cancer cells were grown, and in 5 6-well dishes, unlabeled cancer cells alone were grown. For each 6-wells 100 μl of selected phage from round 1 were blocked using 900 μl 5% MPBS. Cells were washed with 1 ml Cell Dissociation buffer/Hank's balanced salt solution (BSS), and then washed with 1 ml 0.25% trypsin. Cells were digested for 15 min with 0.5 ml 0.25% trypsin at 37° C. MSC and GFP-labeled PC3 cells were combined and counted, then pelleted and washed in MPBS. One×$10^6$ cells were pelleted and resuspended in phage-MPBS. Cells were incubated with phage display library for 10 min at 37° C., followed by 1 hour on ice. Phage-bound cells were washed with MPBS, then washed with PBS, and were resuspended at 1×$10^6$ cells/ml in PBS. A 1× Propidium iodide solution was added and cells were sorted for GFP expression and collected in 200 μl RPMI media (Gibco BRL). Cells were pelleted and phage in each well were eluted using 400 μl 0.1 M glycine pH 2.2 for 15 min at ambient temperature. The elution reaction was stopped using 80 μl 1.5M Tris pH8.8, and 4.5 ml of freshly grown TG1 was added directly to each well.

For subcloning, the 5 ml of TG1 and eluted phage solution was incubated for 45 min at 37° C. without shaking. A 200 μl aliquot was saved for determination of output titre, and the remaining 4.8 ml of infected bacteria was used to inoculate 100 ml 2×YT with Cm34. Cultures were grown overnight at 37° C. DNA from the phagemids was then prepared using Qiagen midi or maxiprep kits according to the manufacturer's directions.

For purification of antigens recognized by a single chain variable antibody region (scfv), six sets of twenty 15 cm plates treated with biotinylated PC3-GFP were prepared. On each set of twenty 15 cm plates, cells were dislodged with PBS containing 10 mM EDTA. Cells were then pelleted and resuspended in 4 ml of a solution containing 10 mM Tris pH 7.5, 1.5 mM $MgCl_2$, and 2× of a protease inhibitor cocktail, and kept on ice for 20 min. Cell extracts were made using a 7 ml dounce, pestle B, and centrifuged for 10 min at 1400 RPM. The supernatant was collected and nuclear pellet resuspended with 3 ml of the same buffer and re-centrifuged. The second supernatant was combined with the 15 supernatant and layered in an SW40 centrifuge tube over 4-5 ml of a solution of 2 M sucrose, 10 mM Tris pH 7.5, 1.5 mM $MgCl_2$, and 2× protease inhibitors. This layered sucrose solution was centrifuged at 35,000 RPM for 20 min, the supernatant discarded and the membrane pad isolated and snap frozen in liquid nitrogen. A total of six preparations were thus made. Each prep was then solubilized in 3 ml of a solution of 20 mM Tris pH 7.5, 225 mM NaCl, 0.75% SDS, 1.5% NP40, and 1× protease inhibitors. The solubilized membrane pad preparations were sonicated with a probe sonicator at 4° C. for 2 min, pulsing 50% of the time and holding on ice between sonications. Sonicated preps were then centrifuged at 100,000×g for 20 min and the six preps were pooled into 18 ml, which was diluted to 90 ml with a solution of 20 mM Tris pH 7.5, 150 mM NaCl, 0.5% NP40.

To purify the antigen recognized by the scfv, an affinity resin was made by coupling the scfv to M2-agarose. Two mg of scfv in PBS was mixed with a 1 ml slurry of M2-agarose resin (Sigma catalog number A222). The mixture was rotated for 1-12 hours at 4° C. and then washed 5× with 200 mM triethanolamine, pH 8.2. A 2 ml solution of 20 mM dimethyl Pimelimidate (Pierce or Sigma) in 200 mM triethanolamine, pH 8.2 was then prepared and added immediately to the M2-scfv mixture. The mixture with the crosslinking agent was incubated with rocking for 45 min at room temp. The DPMI solution was removed after pelleting the resin and the resin was resuspended in 2 ml of 20 mM ethanolamine and was incubated with rocking for 1 hr at room temperature. The resin was then washed with PBS containing 0.02% Sodium Azide, resuspended in 2 ml PBS with 0.02% Sodium Azide, and stored at −80° C.

The M2-agarose-scfv resin was washed 4 times in buffer containing 20 mM Tris pH7.5, 165 mM NaCl, 0.15% SDS and 0.7% NP40. The resin was then mixed in batch with 10 ml of the solubilized membrane prep. The mixture was rotated for 2 hours at 4° C. The M2-agarose-scfv resin was transferred to a 1.5 ml Eppendorf tube and washed 5 times with 1 ml of a buffer containing 20 mM Tris pH 7.5, 500 mM NaCl and 0.5% NP40. The resin was washed one more time with 1 ml of a buffer containing 20 mM Tris pH 7.5, 150 mM NaCl and 0.5% NP40. The resin was then pelleted and eluted by boiling in 300 μl 0.5% SDS, 20 mM Tris pH 8.8. The eluate was lyophilized and stored at −80° C. The lyophilized antigen was resuspended in 25 μl of 10% glycerol, 0.01% phenol red (w/v), DTT (0.04M) and was electrophoresed on an acrylamide gel and stained with Coomassie blue. The appropriate band was excised and subjected to peptide mass spectrometry analysis. The heavy chain sequence unique to Scfv7 was determined to be: INGMSSYIFFDV (SEQ ID NO: 7)

Example 7

Identification of Modulators of Bone Metastasis or SREs

To identify modulators of bone metastasis and/or SREs, candidate compounds are contacted with a co-culture of host cells and cancer cells. Candidate compounds are added to the co-culture of cells at a concentration from about 1 picomolar to about 5 M. In parallel, a control co-culture is allowed to incubate without the candidate compound. After each day, biological markers of bone metastasis or SREs are measured to determine if the candidate compounds are modulators of bone metastasis and/or of SREs. The cell's RNA, DNA, and proteins are isolated to identify the genetic profile of the cells. The genetic profile is compared to the control profile. A change indicative of bone metastasis and/or of SREs is indicative of a modulator of bone metastasis and/or of SREs.

Example 8

EphA2 Antisense Inhibits the Osteoblastic Response

On day 1 PC3 cells were plated at a density of 16,000 cells per $cm^2$ in RPMI with 10% fetal calf serum (FCS) and 1× Pen/Strep. On day 2 cells were either untreated or were transfected with antisense oligonucleotides to EphA2 or with reverse control oligonucleotides. On day 3, the media was changed to osteogenic media and mesenchymal stem cells were added to the culture at a density of 10,000 cells/$cm^2$. The cultures were incubated for another 3 days at 37° C. in 5% $CO_2$. On the third day cells were either fixed and stained for alkaline phosphatase or lysed for quantitative alkaline phosphatase assay. As depicted in FIG. 9, the results showed a decreased in alkaline phosphatase staining and quantitative assay in the presence of the antisense oligonucleotide.

Example 9

EphA2 Antisense Oligonucleotides Inhibit PC3 Cell Growth in Matrigel™

PC3 cells were treated with antisense or reverse control oligonucleotides to EphA2 then plated on Matrigel™ with a 3% Matrigel™ overlay. As depicted in FIG. 13, antisense oligonucleotides inhibited the growth of the PC3 cells, whereas the control oligonucleotide did not.

The effect of EphA2 gene expression upon anchorage-independent cell growth of PC-3 cells was measured by colony formation in Matrigel. Matrigel assays were performed by first coating a non-tissue culture treated plate with PolyHEMA to prevent cells from attaching to the plate. Non-transfected cells were harvested using trypsin and washing twice in media. The cells were counted using a hemacytometer and resuspended to $10^4$ cells per ml in media. Fifty μl aliquots were placed in polyHEMA coated 96-well plates and transfected. For each transfection mixture, a carrier molecule, preferably a lipitoid or cholesteroid, was prepared to a working concentration of 0.5 nM in water, sonicated to yield a uniform solution, and filtered through a 0.45 μm PVDF membrane. The antisense or control oligonucleotide was then prepared to a working concentration of 100 mM in sterile Millipore water. The oligonucleotides were further diluted in OptiMEM™ (Gibco/BRL) in a microfuge tube to 2 μM, or approximately 20 μg oligo/ml of OptiMEM™. In a separate microfuge tube, lipitoid or cholesteroid, typically in the amount of about 1.5-2 nmol lipitoid/1 g antisense oligonucleotide, was diluted in the same volume of OptiMEM™ used to dilute the oligonucleotide. The diluted antisense oligonucleotide was immediately added to the diluted lipitoid and mixed by pipetting up and down. Oligonucleotide was added to the cells to a final concentration of about 300 nM. Following transfection at 37° C. for about 30 minutes, the cells were transferred to a 96-well tissue culture plate coated with 50 μl of Matrigel. The cells were allowed to settle on the Matrigel, then a 3% Matrigel overlay was added on top of the cell layer. Colonies formed in about 7 days, then pictures were taken for a read-out of growth. Separate experiments were performed using a 3-dimensional Matrigel culture of cells as described previously (Peterson et al., Proc. Natl. Acad. Sci. USA 89:9064-9068).

Example 10

EphA2 Antisense Oligonucleotides Inhibit Soft Agar Growth of PC3 Cells

PC3 cells were treated with antisense or reverse control oligonucleotides to EphA2. The cells were plated in 0.35% soft agar and growth quantitated using Alamar Blue after 7 days in culture.

The effect of EphA2 gene expression upon anchorage-independent cell growth of PC3 cells was measured by colony formation in soft agar. Soft agar assays were performed by first coating a non-tissue culture treated plate with PolyHEMA to prevent cells from attaching to the plate. Non-transfected cells were harvested using trypsin and washing twice in media. The cells were counted using a hemacytometer and resuspended to $10^4$ cells per ml in media. Fifty μl aliquots were placed in polyHEMA coated 96-well plates and transfected. For each transfection mixture, a carrier molecule, preferably a lipitoid or cholesteroid, was prepared to a working concentration of 0.5 nM in water, sonicated to yield a uniform solution, and filtered through a 0.45 μm PVDF membrane. The antisense or control oligonucleotide was then prepared to a working concentration of 100 mM in sterile Millipore water. The oligonucleotides were further diluted in OptiMEM™ (Gibco/BRL) in a microfuge tube to 2 μM, or approximately 20 μg oligo/ml of OptiMEM™. In a separate microfuge tube, lipitoid or cholesteroid, typically in the amount of about 1.5-2 nmol lipitoid/μg antisense oligonucleotide, was diluted in the same volume of OptiMEM™ used to dilute the oligonucleotide. The diluted antisense oligonucleotide was immediately added to the diluted lipitoid and mixed by pipetting up and down. Oligonucleotide was added to the cells to a final concentration of about 300 nM. Following transfection at 37° C. for about 30 minutes, 3% GTG agarose was added to the cells for a final concentration of 0.35% agarose by pipetting up and down. After the cell layer agar solidified, 100 μl of media was dribbled on top of each well. Colonies formed in about 7 days. For a read-out of growth, 20 μl of Alamar Blue was added to each well and the plate was shaken for about 15 minutes. Fluorescence readings (530 nm excitation/590 nm emission) were taken after incubation for 6-24 hours.

The data presented in FIG. 14 shows that the application of EphA2 antisense oligonucleotides to PC3 cells results in inhibition of colony formation and shows that EphA2 plays a role in anchorage-independent cell growth. Oligonucleotides used had the following sequences:

```
CHIR-221-4 (antisense)
GCCGCACCCCAATCCTCTTGATGT           (SEQ ID NO: 3)

CHIR-221-4RC (reverse control)
TGTAGTTCTCCTAACCCCACGCCG.          (SEQ ID NO: 4)
```

Those antisense oligonucleotides that result in inhibition of colony formation of PC3 cells indicate that EphA2 plays a role in production or maintenance of the metastatic phenotype or is involved in SREs.

Other antisense oligonucleotides useful in the present invention include, for example, those set forth in Table 1, below:

TABLE 1

| SEQUENCE | SEQ ID NO: |
|---|---|
| CGGCATAGTAGAGGTTGAAAGTCTC | 72 |
| CGCAGGTGACGCTGTAGACAATGT | 73 |
| TGGATGGATCTCGGTAGTGAACTTC | 74 |
| ACTCTCCTGCTCCGATCACCTTCT | 75 |
| TGTATTTGGAGATGACGCCCTCTAG | 76 |
| CCAGGTTGCTGTTGACGAGGATGT | 77 |
| ATCCTCTTGATGTCGTCGTTGGTC | 78 |
| TCCTATATGTCTGTCCGAAGGCTGT | 79 |
| TCTCACCCAGTCAAGTTCACAGTCT | 80 |

Example 11

Methods of Detecting EphA2 Tumors

Total RNA from normal tissues from multiple individuals was pooled, reverse transcribed and subjected to quantitative PCR using primers to EphA2. Amplified RNA from LCM dissected tissue from six cancer and peritumoral normal tissue was reverse transcribed and subjected to quantitative PCR using primers to EphA2. As shown in FIG. 12, mRNA levels in the cancer were found to be approximately twice as high as the peritumoral levels. EphA2 levels in colon cancer samples appeared to be about 2 fold higher than in normal samples.

Example 12

Antisense Regulation of Gene Expression

The expression of the differentially expressed genes represented by the polynucleotides in the cancerous cells can be analyzed using antisense knockout technology to confirm the role and function of the gene product in tumorigenesis, e.g., in promoting a metastatic phenotype.

A number of different oligonucleotides complementary to the mRNA generated by the differentially expressed genes identified herein can be designed as potential antisense oligonucleotides, and tested for their ability to suppress expression of the genes. Sets of antisense oligomers specific to each candidate target are designed using the sequences of the polynucleotides corresponding to a differentially expressed gene and the software program HYBsimulator Version 4 (available for Windows 95/Windows NT or for Power Macintosh, RNAture, Inc. 1003 Health Sciences Road, West, Irvine, Calif. 92612 USA). Factors that are considered when designing antisense oligonucleotides include: 1) the secondary structure of oligonucleotides; 2) the secondary structure of the target gene; 3) the specificity with no or minimum cross-hybridization to other expressed genes; 4) stability; 5) length and 6) terminal GC content. The antisense oligonucleotide is designed so that it will hybridize to its target sequence under conditions of high stringency at physiological temperatures (e.g., an optimal temperature for the cells in culture to provide for hybridization in the cell, e.g., about 37° C.), but with minimal formation of homodimers.

Using the sets of oligomers and the HYBsimulator program, three to ten antisense oligonucleotides and their reverse controls are designed and synthesized for each candidate mRNA transcript, which transcript is obtained from the gene corresponding to the target polynucleotide sequence of interest. Once synthesized and quantitated, the oligomers are screened for efficiency of a transcript knock-out in a panel of cancer cell lines. The efficiency of the knock-out is determined by analyzing mRNA levels using lightcycler quantification. The oligomers that resulted in the highest level of transcript knock-out, wherein the level was at least about 50%, preferably about 80-90%, up to 95% or more up to undetectable message, are selected for use in a cell-based proliferation assay, an anchorage independent growth assay, and a Matrigel assay.

The ability of each designed antisense oligonucleotide to inhibit gene expression is tested through transfection into LNCaP, PC3, 22Rv1, MDA-PCA-2b, or DU145 prostate carcinoma cells, MDA231 breast cancer cells, or HCT116 colon cancer cells. For each transfection mixture, a carrier molecule (such as a lipid, lipid derivative, lipid-like molecule, cholesterol, cholesterol derivative, or cholesterol-like molecule) is prepared to a working concentration of 0.5 mM in water, sonicated to yield a uniform solution, and filtered through a 0.45 μm PVDF membrane. The antisense or control oligonucleotide is then prepared to a working concentration of 100 μM in sterile Millipore water. The oligonucleotide is further diluted in OptiMEM™ (Gibco/BRL), in a microfuge tube, to 2 μM, or approximately 20 μg oligo/ml of OptiMEM™. In a separate microfuge tube, the carrier molecule, typically in the amount of about 1.5-2 nmol carrier/μg antisense oligonucleotide is diluted into the same volume of OptiMEM™ used to dilute the oligonucleotide. The diluted antisense oligonucleotide is immediately added to the diluted carrier and mixed by pipetting up and down. Oligonucleotide is added to the cells to a final concentration of 300 nM.

The level of target mRNA that corresponds to a target gene of interest in the transfected cells is quantitated in the cancer cell lines using the Roche LightCycler™ realtime PCR machine. Values for the target mRNA are normalized versus an internal control (e.g., beta-actin). For each 20 μl reaction, extracted RNA (generally 0.2-1 μg total) is placed into a sterile 0.5 or 1.5 ml microcentrifuge tube, and water is added to a total volume of 12.5 μl. To each tube is added 7.5 μl of a buffer/enzyme mixture, prepared by mixing (in the order listed) 2.5 μl $H_2O$, 2.0 μl 10× reaction buffer, 10 μl oligo dT (20 pmol), 1.0 μl dNTP mix (10 mM each), 0.5 μl RNAsin® (20 u) (Ambion, Inc., Hialeah, Fla.), and 0.5 μl MMLV reverse transcriptase (50 u) (Ambion, Inc.). The contents are mixed by pipetting up and down, and the reaction mixture is incubated at 42° C. for 1 hour. The contents of each tube are centrifuged prior to amplification.

An amplification mixture is prepared by mixing in the following order: 1×PCR buffer II, 3 mM $MgCl_2$, 140 μM each dNTP, 0.175 μmol each oligo, 1:50,000 dil of SYBR® Green, 0.25 mg/ml BSA, 1 unit Taq polymerase, and $H_2O$ to 20 μl. (PCR buffer II is available in 10× concentration from Perkin-Elmer, Norwalk, Conn.). In IX concentration it contains 10 mM Tris pH 8.3 and 50 mM KCl. SYBR® Green (Molecular Probes, Eugene, Oreg.) is a dye which fluoresces when bound to double stranded DNA. As double stranded PCR product is produced during amplification, the fluorescence from SYBR® Green increases. To each 20 μl aliquot of amplification mixture, 2 μl of template RT is added, and amplification is carried out according to standard protocols. The results are expressed as the percent decrease in expression of the corresponding gene product relative to non-transfected cells, vehicle-only transfected (mock-transfected) cells, or cells transfected with reverse control oligonucleotides.

Example 13

Effect of Expression on Proliferation

The effect of gene expression on the inhibition of cell proliferation can be assessed in metastatic breast cancer cell lines (MDA-MB-231 or MDA231 ("231")); SW620 colon colorectal carcinoma cells; SKOV3 cells (a human ovarian carcinoma cell line); or LNCAP, PC3, 22Rv1, MDA-PCA-2b, or DU145 prostate cancer cells.

Cells are plated to a density that will be about 80-95% confluent after days in 96-well dishes. Antisense or reverse control oligonucleotide is diluted to 2 μM in OptiMEM™. The oligonucleotide-OptiMEM™ can then be added to a delivery vehicle, which delivery vehicle can be selected so as to be optimized for the particular cell type to be used in the assay. The oligo/delivery vehicle mixture is then further diluted into medium with serum on the cells. The final concentration of oligonucleotide for all experiments can be about 300 nM.

Antisense oligonucleotides are prepared as described above. Cells are transfected from about 4 hours to overnight at 37° C. and the transfection mixture is replaced with fresh medium. Transfection is carried out as described above.

Those antisense oligonucleotides that result in inhibition of proliferation of SW620 cells indicate that the corresponding gene plays a role in production or maintenance of the cancerous phenotype in cancerous colon cells. Those antisense oligonucleotides that inhibit proliferation in SKOV3 cells represent genes that play a role in production or maintenance of the cancerous phenotype in cancerous ovarian cells. Those antisense oligonucleotides that result in inhibition of proliferation of MDA231 cells indicate that the corresponding gene plays a role in production or maintenance of the cancerous phenotype in cancerous breast cells. Those antisense oligonucleotides that inhibit proliferation in LNCAP, PC3, 22Rv1, MDA-PCA-2b, or DUI45 cells represent genes that play a role in production or maintenance of the cancerous phenotype in cancerous prostate cells.

Example 14

EphA2 Epitopes

Linear epitopes of EphA2 for antibody recognition and preparation can be identified by any of numerous methods known in the art. Some example methods include probing antibody-binding ability of peptides derived from the amino acid sequence of the antigen. Binding can be assessed by using BIACORE or ELISA methods. Other techniques include exposing peptide libraries on planar solid support ("chip") to antibodies and detecting binding through any of multiple methods used in solid-phase screening. Additionally, phage display can be used to screen a library of peptides with selection of epitopes after several rounds of biopanning.

Table 2 below provides regions of EphA2 (SEQ ID NO:6) that have been identified as linear epitopes suitable for recognition by anti-EphA2 antibodies.

TABLE 2

| ECD Name | Mapped amino acid sequence location | Mapped epitope location | Length | SEQ ID NO: | SEQUENCE |
|---|---|---|---|---|---|
| EphA2#1 | 156-166 | 156-163 | 8 | 12 | FEARHVKL |
| EphA2#1 | 156-166 | 157-164 | 8 | 13 | EARHVKLN |
| EphA2#1 | 156-166 | 158-165 | 8 | 14 | ARHVKLNV |
| EphA2#1 | 156-166 | 159-166 | 8 | 15 | RHVKLNVE |
| EphA2#1 | 156-166 | 156-164 | 9 | 16 | FEARHVKLN |
| EphA2#1 | 156-166 | 157-165 | 9 | 17 | EARHVKLNV |
| EphA2#1 | 156-166 | 158-166 | 9 | 18 | ARHVKLNVE |
| EphA2#1 | 156-166 | 156-165 | 10 | 19 | FEARHVKLNV |
| EphA2#1 | 156-166 | 157-166 | 10 | 20 | EARHVKLNVE |
| EphA2#1 | 156-166 | 156-166 | 11 | 21 | FEARHVKLNVE |
| EphA2#2 | 188-203 | 188-195 | 8 | 22 | CVALLSVR |
| EphA2#2 | 188-203 | 189-196 | 8 | 23 | VALLSVRV |
| EphA2#2 | 188-203 | 190-197 | 8 | 24 | ALLSVRVY |
| EphA2#2 | 188-203 | 191-198 | 8 | 25 | LLSVRVYY |
| EphA2#2 | 188-203 | 192-199 | 8 | 26 | LSVRVYYK |
| EphA2#2 | 188-203 | 193-200 | 8 | 27 | SVRVYYKK |
| EphA2#2 | 188-203 | 194-201 | 8 | 28 | VRVYYKKC |
| EphA2#2 | 188-203 | 195-202 | 8 | 29 | RVYYKKCP |
| EphA2#2 | 188-203 | 196-203 | 8 | 30 | VYYKKCPE |
| EphA2#2 | 188-203 | 188-196 | 9 | 31 | CVALLSVRV |
| EphA2#2 | 188-203 | 189-197 | 9 | 32 | VALLSVRVY |
| EpbA2#2 | 188-203 | 190-198 | 9 | 33 | ALLSVRVYY |
| EphA2#2 | 188-203 | 191-199 | 9 | 34 | LLSVRVYYK |
| EphA2#2 | 188-203 | 192-200 | 9 | 35 | LSVRVYYKK |
| EphA2#2 | 188-203 | 193-201 | 9 | 36 | SVRVYYKKC |
| EpbA2#2 | 188-203 | 194-202 | 9 | 37 | VRVYYKKCP |
| EphA2#2 | 188-203 | 195-203 | 9 | 38 | RVYYKKCPE |
| EphA2#2 | 188-203 | 188-197 | 10 | 39 | CVALLSVRVY |
| EphA2#2 | 188-203 | 189-198 | 10 | 40 | VALLSVRVYY |
| EphA2#2 | 188-203 | 190-199 | 10 | 41 | ALLSVRVYYK |

TABLE 2-continued

| ECD Name | Mapped amino acid sequence location | Mapped epitope location | Length | SEQ ID NO: | SEQUENCE |
|---|---|---|---|---|---|
| EphA2#2 | 188-203 | 191-200 | 10 | 42 | LLSVRVYYKK |
| EphA2#2 | 188-203 | 192-201 | 10 | 43 | LSVRVYYKKC |
| EphA2#2 | 188-203 | 193-202 | 10 | 44 | SVRVYYKKCP |
| EphA2#2 | 188-203 | 194-203 | 10 | 45 | VRVYYKKCPE |
| EphA2#2 | 188-203 | 188-198 | 11 | 46 | CVALLSVRVYY |
| EphA2#2 | 188-203 | 189-199 | 11 | 47 | VALLSVRVYYK |
| EphA2#2 | 188-203 | 190-200 | 11 | 48 | ALLSVRVYYKK |
| EphA2#2 | 188-203 | 191-201 | 11 | 49 | LLSVRVYYKKC |
| EphA2#2 | 188-203 | 192-202 | 11 | 50 | LSVRVYYKKCP |
| EphA2#2 | 188-203 | 193-203 | 11 | 51 | SVRVYYKKCPE |
| EphA2#2 | 188-203 | 188-199 | 12 | 52 | CVALLSVRVYYK |
| EphA2#2 | 188-203 | 189-200 | 12 | 53 | VALLSVRVYYKK |
| EphA2#2 | 188-203 | 190-201 | 12 | 54 | ALLSVRVYYKKC |
| EphA2#2 | 188-203 | 191-202 | 12 | 55 | LLSVRVYYKKCP |
| EphA2#2 | 188-203 | 192-203 | 12 | 56 | LSVRVYYKKCPE |
| EphA2#3 | 559-570 | 559-566 | 8 | 57 | HRRRKNQR |
| EphA2#3 | 559-570 | 560-567 | 8 | 58 | RRRKNQRA |
| EphA2#3 | 559-570 | 561-568 | 8 | 59 | RRKNQRAR |
| EphA2#3 | 559-570 | 562-569 | 8 | 60 | RKNQRARQ |
| EphA2#3 | 559-570 | 563-570 | 8 | 61 | KNQRARQS |
| EphA2#3 | 559-570 | 559-567 | 9 | 62 | HRRRKNQRA |
| EphA2#3 | 559-570 | 560-568 | 9 | 63 | RRRKNQRAR |
| EphA2#3 | 559-570 | 561-569 | 9 | 64 | RRKNQRARQ |
| EphA2#3 | 559-570 | 562-570 | 9 | 65 | RKNQRARQS |
| EphA2#3 | 559-570 | 559-568 | 10 | 66 | HRRRKNQRAR |
| EphA2#3 | 559-570 | 560-569 | 10 | 67 | RRRKNQRARQ |
| EpbA2#3 | 559-570 | 561-570 | 10 | 68 | RRKNQRARQS |
| EphA2#3 | 559-570 | 559-569 | 11 | 69 | HRRRKNQRARQ |
| EphA2#3 | 559-570 | 560-570 | 11 | 70 | RRRKNQRARQS |
| EphA2#3 | 559-570 | 559-570 | 12 | 71 | HRRRKNQRARQS |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the present invention.

We claim:

1. A method for determining the susceptibility of a cancer patient to an osteoblastic response in mesenchymal stem cells comprising detecting evidence of EphA2 expression in a patient's cancer sample, wherein the sample comprises cancer and host cells and wherein evidence of EphA2 expression is indicative of the patient's susceptibility to an osteoblastic response in mesenchymal stem cells.

2. The method of claim 1 wherein the cancer sample is co-cultured with host cells from said patient.

3. The method of claim 1 wherein evidence of EphA2 expression is detected by measuring EphA2 RNA.

4. The method of claim 1 wherein evidence of EphA2 expression is detected by measuring EphA2 expression products.

5. The method of claim 1 wherein the patient's cancer sample comprises cancer cells selected from the group consisting of breast, prostate, colon, melanoma, thyroid, and ovarian cells.

* * * * *

UNITED STATES PATENT AND TRADEMARK OFFICE

CERTIFICATE OF CORRECTION

PATENT NO. : 8,012,681 B2
APPLICATION NO. : 10/556765
DATED : September 6, 2011
INVENTOR(S) : Deborah Lee Zimmerman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 862 days.

Signed and Sealed this
Twenty-first Day of February, 2012

David J. Kappos
*Director of the United States Patent and Trademark Office*

SEQUENCE LISTING

<160> NUMBER OF SEQ ID NOS: 80

<210> SEQ ID NO 1
<211> LENGTH: 3921
<212> TYPE: DNA
<213> ORGANISM: Homo sapiens

<400> SEQUENCE: 1
cggaagttgc gcgcaggccg gcgggcggga gcggacaccg aggccggcgt gcaggcgtgc 60
gggtgtgcgg gagccgggct cggggggatc ggaccgagag cgagaagcgc ggcatggagc 120
tccaggcagc ccgcgcctgc ttcgccctgc tgtggggctg tgcgctggcc gcggccgcgg 180
cggcgcaggg caaggaagtg gtactgctgg actttgctgc agctggaggg gagctcggct 240
ggctcacaca cccgtatggc aaagggtggg acctgatgca gaacatcatg aatgacatgc 300
cgatctacat gtactccgtg tgcaacgtga tgtctggcga ccaggacaac tggctccgca 360
ccaactgggt gtaccgagga gaggctgagc gtaacaactt tgagctcaac tttactgtac 420
gtgactgcaa cagcttccct ggtggcgcca gctcctgcaa ggagactttc aacctctact 480
atgccgagtc ggacctggac tacggcacca acttccagaa gcgcctgttc accaagattg 540
acaccattgc gcccgatgag atcaccgtca gcagcgactt cgaggcacgc cacgtgaagc 600
tgaacgtgga ggagcgctcc gtggggccgc tcacccgcaa aggcttctac ctggccttcc 660

```
aggatatcgg tgcctgtgtg gcgctgctct ccgtccgtgt ctactacaag aagtgccccg    720
agctgctgca gggcctggcc cacttccctg agaccatcgc cggctctgat gcaccttccc    780
tggccactgt ggccggcacc tgtgtggacc atgccgtggt gccaccgggg ggtgaagagc    840
cccgtatgca ctgtgcagtg gatggcgagt ggctggtgcc cattgggcag tgcctgtgcc    900
aggcaggcta cgagaaggtg gaggatgcct gccaggcctg ctcgcctgga ttttttaagt    960
ttgaggcatc tgagagcccc tgcttggagt gccctgagca cacgctgcca tcccctgagg   1020
gtgccacctc ctgcgagtgt gaggaaggct tcttccgggc acctcaggac ccagcgtcga   1080
tgccttgcac acgacccccct tccgccccac actacctcac agccgtgggc atgggtgcca   1140
aggtggagct gcgctggacg ccccctcagg acagcggggg ccgcgaggac attgtctaca   1200
gcgtcacctg cgaacagtgc tggcccgagt ctggggaatg cgggccgtgt gaggccagtg   1260
tgcgctactc ggagcctcct cacggactga cccgcaccag tgtgacagtg agcgacctgg   1320
agccccacat gaactacacc ttcaccgtgg aggcccgcaa tggcgtctca ggcctggtaa   1380
ccagccgcag cttccgtact gccagtgtca gcatcaacca gacagagccc cccaaggtga   1440
ggctggaggg ccgcagcacc acctcgctta gcgtctcctg gagcatcccc ccgccgcagc   1500
agagccgagt gtggaagtac gaggtcactt accgcaagaa gggagactcc aacagctaca   1560
atgtgcgccg caccgagggt ttctccgtga ccctggacga cctggcccca gacaccacct   1620
acctggtcca ggtgcaggca ctgacgcagg agggccaggg ggccggcagc aaggtgcacg   1680
aattccagac gctgtccccg gagggatctg gcaacttggc ggtgattggc ggcgtggctg   1740
tcggtgtggt cctgcttctg gtgctggcag gagttggctt ctttatccac cgcaggagga   1800
agaaccagcg tgcccgccag tccccggagg acgtttactt ctccaagtca gaacaactga   1860
agcccctgaa gacatacgtg gacccccaca catatgagga ccccaaccag gctgtgttga   1920
agttcactac cgagatccat ccatcctgtg tcactcggca gaaggtgatc ggagcaggag   1980
agtttgggga ggtgtacaag ggcatgctga agacatcctc ggggaagaag gaggtgccgg   2040
tggccatcaa gacgctgaaa gccggctaca cagagaagca gcgagtggac ttcctcggcg   2100
aggccggcat catgggccag ttcagccacc acaacatcat ccgcctagag ggcgtcatct   2160
ccaaatacaa gcccatgatg atcatcactg agtacatgga gaatggggcc ctggacaagt   2220
tccttcggga gaaggatggc gagttcagcg tgctgcagct ggtgggcatg ctgcggggca   2280
tcgcagctgg catgaagtac ctggccaaca tgaactatgt gcaccgtgac ctggctgccc   2340
gcaacatcct cgtcaacagc aacctggtct gcaaggtgtc tgactttggc ctgtcccgcg   2400
tgctggagga cgaccccgag gccacctaca ccaccagtgg cggcaagatc cccatccgct   2460
ggaccgcccc ggaggccatt tcctaccgga agttcacctc tgccagcgac gtgtggagct   2520
ttggcattgt catgtgggag gtgatgacct atggcgagcg gccctactgg gagttgtcca   2580
accacgaggt gatgaaagcc atcaatgatg gcttccggct ccccacaccc atggactgcc   2640
cctccgccat ctaccagctc atgatgcagt gctggcagca ggagcgtgcc cgccgcccca   2700
agttcgctga catcgtcagc atcctggaca agctcattcg tgcccctgac tccctcaaga   2760
ccctggctga ctttgacccc cgcgtgtcta tccggctccc cagcacgagc ggctcggagg   2820
gggtgccctt ccgcacggtg tccgagtggc tggagtccat caagatgcag cagtatacgg   2880
agcacttcat ggcggccggc tacactgcca tcgagaaggt ggtgcagatg accaacgacg   2940
acatcaagag gattggggtg cggctgcccg gccaccagaa gcgcatcgcc tacagcctgc   3000
tgggactcaa ggaccaggtg aacactgtgg ggatccccat ctgagcctcg acagggcctg   3060
```

```
gagccccatc ggccaagaat acttgaagaa acagagtggc ctccctgctg tgccatgctg   3120

ggccactggg gactttattt atttctagtt ctttcctccc cctgcaactt ccgctgaggg   3180

gtctcggatg acaccctggc ctgaactgag gagatgacca gggatgctgg gctgggccct   3240

ctttccctgc gagacgcaca cagctgagca cttagcaggc accgccacgt cccagcatcc   3300

ctggagcagg agccccgcca cagccttcgg acagacatat aggatattcc caagccgacc   3360

ttccctccgc cttctcccac atgaggccat ctcaggagat ggagggcttg gcccagcgcc   3420

aagtaaacag ggtacctcaa gccccatttc ctcacactaa gagggcagac tgtgaacttg   3480

actgggtgag acccaaagcg gtccctgtcc ctctagtgcc ttctttagac cctcgggccc   3540

catcctcatc cctgactggc caaacccttg ctttcctggg cctttgcaag atgcttggtt   3600

gtgttgaggt ttttaaatat atattttgta ctttgtggag agaatgtgtg tgtgtggcag   3660

ggggccccgc cagggctggg gacagagggt gtcaaacatt cgtgagctgg ggactcaggg   3720

accggtgctg caggagtgtc ctgcccatgc cccagtcggc cccatctctc atccttttgg   3780

ataagtttct attctgtcag tgttaaagat tttgttttgt tggacatttt tttcgaatct   3840

taatttatta ttttttttat atttattgtt agaaaatgac ttatttctgc tctggaataa   3900

agttgcagat gattcaaacc g                                              3921
```

<210> SEQ ID NO 2
<211> LENGTH: 976
<212> TYPE: PRT
<213> ORGANISM: Homo sapiens

<400> SEQUENCE: 2

```
Met Glu Leu Gln Ala Ala Arg Ala Cys Phe Ala Leu Leu Trp Gly Cys
1               5                   10                  15

Ala Leu Ala Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Asn Asn Phe
                85                  90                  95

Glu Leu Asn Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220
```

-continued

```
Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655
```

```
Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
    930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975
```

<210> SEQ ID NO 3
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 3
gccgcacccc aatcctcttg atgt 24

<210> SEQ ID NO 4
<211> LENGTH: 24
<212> TYPE: DNA
<213> ORGANISM: Artificial Sequence
<220> FEATURE:
<223> OTHER INFORMATION: reverse control oligonucleotide

<400> SEQUENCE: 4
tgtagttctc ctaaccccac gccg 24

<210> SEQ ID NO 5
<211> LENGTH: 3921
<212> TYPE: DNA
<213> ORGANISM: Homo sapiens

<400> SEQUENCE: 5
cggaagttgc gcgcaggccg gcgggcggga gcggacaccg aggccggcgt gcaggcgtgc 60
gggtgtgcgg gagccgggct cggggggatc ggaccgagag cgagaagcgc ggcatggagc 120
tccaggcagc ccgcgcctgc ttcgccctgc tgtggggctg tgcgctggcc gcggccgcgg 180
cggcgcaggg caaggaagtg gtactgctgg actttgctgc agctggaggg gagctcggct 240
ggctcacaca cccgtatggc aaagggtggg acctgatgca gaacatcatg aatgacatgc 300
cgatctacat gtactccgtg tgcaacgtga tgtctggcga ccaggacaac tggctccgca 360
ccaactgggt gtaccgagga gaggctgagc gtaacaactt tgagctcaac tttactgtac 420
gtgactgcaa cagcttccct ggtggcgcca gctcctgcaa ggagactttc aacctctact 480
atgccgagtc ggacctggac tacggcacca acttccagaa gcgcctgttc accaagattg 540
acaccattgc gcccgatgag atcaccgtca gcagcgactt cgaggcacgc cacgtgaagc 600
tgaacgtgga ggagcgctcc gtggggccgc tcacccgcaa aggcttctac ctggccttcc 660
aggatatcgg tgcctgtgtg gcgctgctct ccgtccgtgt ctactacaag aagtgccccg 720
agctgctgca gggcctggcc cacttccctg agaccatcgc cggctctgat gcaccttccc 780
tggccactgt ggccggcacc tgtgtggacc atgccgtggt gccaccgggg ggtgaagagc 840
cccgtatgca ctgtgcagtg gatggcgagt ggctggtgcc cattgggcag tgcctgtgcc 900
aggcaggcta cgagaaggtg gaggatgcct gccaggcctg ctcgcctgga tttttttaagt 960 ttgaggcatc tgagagcccc tgcttggagt gccctgagca cacgctgcca tcccctgagg 1020
gtgccacctc ctgcgagtgt gaggaaggct tcttccgggc acctcaggac ccagcgtcga 1080
tgccttgcac acgacccccct tccgccccac actacctcac agccgtgggc atgggtgcca 1140
aggtggagct gcgctggacg ccccctcagg acagcggggg ccgcgaggac attgtctaca 1200
gcgtcacctg cgaacagtgc tggcccgagt ctggggaatg cgggccgtgt gaggccagtg 1260
tgcgctactc ggagcctcct cacggactga cccgcaccag tgtgacagtg agcgacctgg 1320
agccccacat gaactacacc ttcaccgtgg aggcccgcaa tggcgtctca ggcctggtaa 1380
ccagccgcag cttccgtact gccagtgtca gcatcaacca gacagagccc cccaaggtga 1440
ggctggaggg ccgcagcacc acctcgctta gcgtctcctg gagcatcccc ccgccgcagc 1500
agagccgagt gtggaagtac gaggtcactt accgcaagaa gggagactcc aacagctaca 1560
atgtgcgccg caccgagggt ttctccgtga ccctggacga cctggcccca gacaccacct 1620
acctggtcca ggtgcaggca ctgacgcagg agggccaggg ggccggcagc aaggtgcacg 1680
aattccagac gctgtccccg gagggatctg gcaacttggc ggtgattggc ggcgtggctg 1740
tcggtgtggt cctgcttctg gtgctggcag gagttggctt ctttatccac cgcaggagga 1800
agaaccagcg tgcccgccag tccccggagg acgtttactt ctccaagtca gaacaactga 1860
agcccctgaa gacatacgtg gacccccaca catatgagga ccccaaccag gctgtgttga 1920
agttcactac cgagatccat ccatcctgtg tcactcggca gaaggtgatc ggagcaggag 1980
agtttgggga ggtgtacaag ggcatgctga agacatcctc ggggaagaag gaggtgccgg 2040

```
tggccatcaa gacgctgaaa gccggctaca cagagaagca gcgagtggac ttcctcggcg   2100

aggccggcat catgggccag ttcagccacc acaacatcat ccgcctagag ggcgtcatct   2160

ccaaatacaa gcccatgatg atcatcactg agtacatgga gaatggggcc ctggacaagt   2220

tccttcggga gaaggatggc gagttcagcg tgctgcagct ggtgggcatg ctgcggggca   2280

tcgcagctgg catgaagtac ctggccaaca tgaactatgt gcaccgtgac ctggctgccc   2340

gcaacatcct cgtcaacagc aacctggtct gcaaggtgtc tgactttggc ctgtcccgcg   2400

tgctggagga cgaccccgag gccacctaca ccaccagtgg cggcaagatc cccatccgct   2460

ggaccgcccc ggaggccatt tcctaccgga agttcacctc tgccagcgac gtgtggagct   2520

ttggcattgt catgtgggag gtgatgacct atggcgagcg gccctactgg gagttgtcca   2580

accacgaggt gatgaaagcc atcaatgatg gcttccggct ccccacaccc atggactgcc   2640

cctccgccat ctaccagctc atgatgcagt gctggcagca ggagcgtgcc cgccgcccca   2700

agttcgctga catcgtcagc atcctggaca agctcattcg tgcccctgac tccctcaaga   2760

ccctggctga ctttgacccc cgcgtgtcta tccggctccc cagcacgagc ggctcggagg   2820

gggtgccctt ccgcacggtg tccgagtggc tggagtccat caagatgcag cagtatacgg   2880

agcacttcat ggcggccggc tacactgcca tcgagaaggt ggtgcagatg accaacgacg   2940

acatcaagag gattggggtg cggctgcccg gccaccagaa gcgcatcgcc tacagcctgc   3000

tgggactcaa ggaccaggtg aacactgtgg ggatccccat ctgagcctcg acagggcctg   3060

gagccccatc ggccaagaat acttgaagaa acagagtggc ctccctgctg tgccatgctg   3120

ggccactggg gactttattt atttctagtt ctttcctccc cctgcaactt ccgctgaggg   3180

gtctcggatg acaccctggc ctgaactgag gagatgacca gggatgctgg gctgggccct   3240

ctttccctgc gagacgcaca cagctgagca cttagcaggc accgccacgt cccagcatcc   3300

ctggagcagg agccccgcca cagccttcgg acagacatat aggatattcc caagccgacc   3360

ttccctccgc cttctcccac atgaggccat ctcaggagat ggagggcttg gcccagcgcc   3420

aagtaaacag ggtacctcaa gccccatttc ctcacactaa gagggcagac tgtgaacttg   3480

actgggtgag acccaaagcg gtccctgtcc ctctagtgcc ttctttagac cctcgggccc   3540

catcctcatc cctgactggc caaacccttg ctttcctggg cctttgcaag atgcttggtt   3600

gtgttgaggt ttttaaatat atattttgta ctttgtggag agaatgtgtg tgtgtggcag   3660

ggggccccgc cagggctggg gacagagggt gtcaaacatt cgtgagctgg ggactcaggg   3720

accggtgctg caggagtgtc ctgcccatgc cccagtcggc cccatctctc atccttttgg   3780

ataagtttct attctgtcag tgttaaagat tttgttttgt tggacatttt tttcgaatct   3840

taatttatta ttttttttat atttattgtt agaaaatgac ttatttctgc tctggaataa   3900

agttgcagat gattcaaacc g                                             3921
```

<210> SEQ ID NO 6
<211> LENGTH: 976
<212> TYPE: PRT
<213> ORGANISM: Homo sapiens

<400> SEQUENCE: 6

```
Met Glu Leu Gln Ala Ala Arg Ala Cys Phe Ala Leu Leu Trp Gly Cys
1               5                   10                  15

Ala Leu Ala Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
```

```
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Asn Asn Phe
                85                  90                  95

Glu Leu Asn Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460
```

```
Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895
```

```
Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
    930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975


<210> SEQ ID NO 7
<211> LENGTH: 12
<212> TYPE: PRT
<213> ORGANISM: Artificial Sequence
<220> FEATURE:
<223> OTHER INFORMATION: Heavy chain sequence unique to Scfv7

<400> SEQUENCE: 7

Ile Asn Gly Met Ser Ser Tyr Ile Phe Phe Asp Val
1               5                   10


<210> SEQ ID NO 8
<211> LENGTH: 535
<212> TYPE: PRT
<213> ORGANISM: Homo sapiens

<400> SEQUENCE: 8

Met Glu Leu Gln Ala Ala Arg Ala Cys Phe Ala Leu Leu Trp Gly Cys
1               5                   10                  15

Ala Leu Ala Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Asn Asn Phe
                85                  90                  95

Glu Leu Asn Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
```

```
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu
    530                 535


<210> SEQ ID NO 9
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 9

tcctcttgat gtcgtcgttg gtcat                                            25


<210> SEQ ID NO 10
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 10
```

ccagcagtac cgcttccttg ccctg 25

<210> SEQ ID NO 11
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 11
tggcatgaac ccgggaggca gagc 24

<210> SEQ ID NO 12
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 12

Phe Glu Ala Arg His Val Lys Leu
1 5

<210> SEQ ID NO 13
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 13

Glu Ala Arg His Val Lys Leu Asn
1 5

<210> SEQ ID NO 14
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 14

Ala Arg His Val Lys Leu Asn Val
1 5

<210> SEQ ID NO 15
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 15

Arg His Val Lys Leu Asn Val Glu
1 5

<210> SEQ ID NO 16
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 16

Phe Glu Ala Arg His Val Lys Leu Asn
1 5

<210> SEQ ID NO 17
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 17

Glu Ala Arg His Val Lys Leu Asn Val
1               5

<210> SEQ ID NO 18
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 18

Ala Arg His Val Lys Leu Asn Val Glu
1               5

<210> SEQ ID NO 19
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 19

Phe Glu Ala Arg His Val Lys Leu Asn Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 20

Glu Ala Arg His Val Lys Leu Asn Val Glu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 21

Phe Glu Ala Arg His Val Lys Leu Asn Val Glu
1               5                   10

<210> SEQ ID NO 22
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 22

Cys Val Ala Leu Leu Ser Val Arg
1               5

<210> SEQ ID NO 23

<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 23

Val Ala Leu Leu Ser Val Arg Val
1 5

<210> SEQ ID NO 24
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 24

Ala Leu Leu Ser Val Arg Val Tyr
1 5

<210> SEQ ID NO 25
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 25

Leu Leu Ser Val Arg Val Tyr Tyr
1 5

<210> SEQ ID NO 26
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 26

Leu Ser Val Arg Val Tyr Tyr Lys
1 5

<210> SEQ ID NO 27
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 27

Ser Val Arg Val Tyr Tyr Lys Lys
1 5

<210> SEQ ID NO 28
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 28

Val Arg Val Tyr Tyr Lys Lys Cys
1 5

<210> SEQ ID NO 29
<211> LENGTH: 8
<212> TYPE: PRT

<213> ORGANISM: Artificial Sequence
<220> FEATURE:
<223> OTHER INFORMATION: linear epitope for antibody recognition

<400> SEQUENCE: 29

Arg Val Tyr Tyr Lys Lys Cys Pro
1               5

<210> SEQ ID NO 30
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 30

Val Tyr Tyr Lys Lys Cys Pro Glu
1               5

<210> SEQ ID NO 31
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 31

Cys Val Ala Leu Leu Ser Val Arg Val
1               5

<210> SEQ ID NO 32
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 32

Val Ala Leu Leu Ser Val Arg Val Tyr
1               5

<210> SEQ ID NO 33
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 33

Ala Leu Leu Ser Val Arg Val Tyr Tyr
1               5

<210> SEQ ID NO 34
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 34

Leu Leu Ser Val Arg Val Tyr Tyr Lys
1               5

<210> SEQ ID NO 35
<211> LENGTH: 9
<212> TYPE: PRT
<213> ORGANISM: Artificial Sequence
<220> FEATURE:

<223> OTHER INFORMATION: linear epitope for antibody recognition

<400> SEQUENCE: 35

Leu Ser Val Arg Val Tyr Tyr Lys Lys
1 5

<210> SEQ ID NO 36
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 36

Ser Val Arg Val Tyr Tyr Lys Lys Cys
1 5

<210> SEQ ID NO 37
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 37

Val Arg Val Tyr Tyr Lys Lys Cys Pro
1 5

<210> SEQ ID NO 38
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 38

Arg Val Tyr Tyr Lys Lys Cys Pro Glu
1 5

<210> SEQ ID NO 39
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 39

Cys Val Ala Leu Leu Ser Val Arg Val Tyr
1 5 10

<210> SEQ ID NO 40
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 40

Val Ala Leu Leu Ser Val Arg Val Tyr Tyr
1 5 10

<210> SEQ ID NO 41
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 41

Ala Leu Leu Ser Val Arg Val Tyr Tyr Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 42

Leu Leu Ser Val Arg Val Tyr Tyr Lys Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 43

Leu Ser Val Arg Val Tyr Tyr Lys Lys Cys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 44

Ser Val Arg Val Tyr Tyr Lys Lys Cys Pro
1               5                   10

<210> SEQ ID NO 45
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 45

Val Arg Val Tyr Tyr Lys Lys Cys Pro Glu
1               5                   10

<210> SEQ ID NO 46
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 46

Cys Val Ala Leu Leu Ser Val Arg Val Val Tyr
1               5                   10

<210> SEQ ID NO 47
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 47

```
Val Ala Leu Leu Ser Val Arg Val Val Tyr Lys
1               5                   10


<210> SEQ ID NO 48
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 48

Ala Leu Leu Ser Val Arg Val Val Tyr Lys Lys
1               5                   10


<210> SEQ ID NO 49
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 49

Leu Leu Ser Val Arg Val Val Tyr Lys Lys Cys
1               5                   10


<210> SEQ ID NO 50
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 50

Leu Ser Val Arg Val Val Tyr Lys Lys Cys Pro
1               5                   10


<210> SEQ ID NO 51
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 51

Ser Val Arg Val Val Tyr Lys Lys Cys Pro Glu
1               5                   10


<210> SEQ ID NO 52
<211> LENGTH: 12
<212> TYPE: PRT
<213> ORGANISM: Artificial Sequence
<220> FEATURE:
<223> OTHER INFORMATION: linear epitope for antibody recognition

<400> SEQUENCE: 52

Cys Val Ala Leu Leu Ser Val Arg Val Tyr Tyr Lys
1               5                   10


<210> SEQ ID NO 53
<211> LENGTH: 12
<212> TYPE: PRT
<213> ORGANISM: Artificial Sequence
<220> FEATURE:
<223> OTHER INFORMATION: linear epitope for antibody recognition

<400> SEQUENCE: 53

Val Ala Leu Leu Ser Val Arg Val Tyr Tyr Lys Lys
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: linear epitope for antibody recognition

<400> SEQUENCE: 54

```
Ala Leu Leu Ser Val Arg Val Tyr Tyr Lys Lys Cys
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: linear epitope for antibody recognition

<400> SEQUENCE: 55

```
Leu Leu Ser Val Arg Val Tyr Tyr Lys Lys Cys Pro
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: linear epitope for antibody recognition

<400> SEQUENCE: 56

```
Leu Ser Val Arg Val Tyr Tyr Lys Lys Cys Pro Glu
1               5                   10
```

<210> SEQ ID NO 57
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 57

```
His Arg Arg Arg Lys Asn Gln Arg
1               5
```

<210> SEQ ID NO 58
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 58

```
Arg Arg Arg Lys Asn Gln Arg Ala
1               5
```

<210> SEQ ID NO 59
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 59

```
Arg Arg Lys Asn Gln Arg Ala Arg
1               5
```

<210> SEQ ID NO 60
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 60

Arg Lys Asn Gln Arg Ala Arg Gln
1               5

<210> SEQ ID NO 61
<211> LENGTH: 8
<212> TYPE: PRT
<213> ORGANISM: Artificial Sequence
<220> FEATURE:
<223> OTHER INFORMATION: linear epitope for antibody recognition

<400> SEQUENCE: 61

Lys Asn Gln Arg Ala Arg Gln Ser
1               5

<210> SEQ ID NO 62
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 62

His Arg Arg Arg Lys Asn Gln Arg Ala
1               5

<210> SEQ ID NO 63
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 63

Arg Arg Arg Lys Asn Gln Arg Ala Arg
1               5

<210> SEQ ID NO 64
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 64

Arg Arg Lys Asn Gln Arg Ala Arg Gln
1               5

<210> SEQ ID NO 65
<211> LENGTH: 9
<212> TYPE: PRT
<213> ORGANISM: Artificial Sequence
<220> FEATURE:
<223> OTHER INFORMATION: linear epitope for antibody recognition

<400> SEQUENCE: 65

Arg Lys Asn Gln Arg Ala Arg Gln Ser
1               5

<210> SEQ ID NO 66
<211> LENGTH: 10

<212> TYPE: PRT
<213> ORGANISM: Artificial Sequence
<220> FEATURE:
<223> OTHER INFORMATION: linear epitope for antibody recognition

<400> SEQUENCE: 66

His Arg Arg Arg Lys Asn Gln Arg Ala Arg
1 5 10

<210> SEQ ID NO 67
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 67

Arg Arg Arg Lys Asn Gln Arg Ala Arg Gln
1 5 10

<210> SEQ ID NO 68
<211> LENGTH: 10
<212> TYPE: PRT
<213> ORGANISM: Artificial Sequence
<220> FEATURE:
<223> OTHER INFORMATION: linear epitope for antibody recognition

<400> SEQUENCE: 68

Arg Arg Lys Asn Gln Arg Ala Arg Gln Ser
1 5 10

<210> SEQ ID NO 69
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 69

His Arg Arg Arg Lys Asn Gln Arg Ala Arg Gln
1 5 10

<210> SEQ ID NO 70
<211> LENGTH: 11
<212> TYPE: PRT
<213> ORGANISM: Artificial Sequence
<220> FEATURE:
<223> OTHER INFORMATION: linear epitope for antibody recognition

<400> SEQUENCE: 70

Arg Arg Arg Lys Asn Gln Arg Ala Arg Gln Ser
1 5 10

<210> SEQ ID NO 71
<211> LENGTH: 12
<212> TYPE: PRT
<213> ORGANISM: Artificial Sequence
<220> FEATURE:
<223> OTHER INFORMATION: linear epitope for antibody recognition

<400> SEQUENCE: 71

His Arg Arg Arg Lys Asn Gln Arg Ala Arg Gln Ser
1 5 10

<210> SEQ ID NO 72
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 72
cggcatagta gaggttgaaa gtctc 25

<210> SEQ ID NO 73
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 73
cgcaggtgac gctgtagaca atgt 24

<210> SEQ ID NO 74
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 74
tggatggatc tcggtagtga acttc 25

<210> SEQ ID NO 75
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 75
actctcctgc tccgatcacc ttct 24

<210> SEQ ID NO 76
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 76
tgtatttgga gatgacgccc tctag 25

<210> SEQ ID NO 77
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 77
ccaggttgct gttgacgagg atgt 24

<210> SEQ ID NO 78
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 78
atcctcttga tgtcgtcgtt ggtc 24

-continued

```
<210> SEQ ID NO 79
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 79

tcctatatgt ctgtccgaag gctgt                                        25


<210> SEQ ID NO 80
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 80

tctcacccag tcaagttcac agtct                                        25
```